(12) United States Patent
Uda et al.

(10) Patent No.: US 12,117,451 B2
(45) Date of Patent: Oct. 15, 2024

(54) TEST PIECE FOR ALBUMIN MEASUREMENT

(71) Applicant: ARKRAY, Inc., Kyoto (JP)

(72) Inventors: Keigo Uda, Kyoto (JP); Miki Inatome, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 105 days.

(21) Appl. No.: 17/535,925

(22) Filed: Nov. 26, 2021

(65) Prior Publication Data

US 2022/0170928 A1  Jun. 2, 2022

(30) Foreign Application Priority Data

Nov. 27, 2020 (JP) ................................ 2020-197352
Jul. 12, 2021 (JP) ................................ 2021-114976
Nov. 22, 2021 (JP) ................................ 2021-189688

(51) Int. Cl.
*G01N 33/68* (2006.01)
*G01N 21/77* (2006.01)
*G01N 21/78* (2006.01)

(52) U.S. Cl.
CPC ......... *G01N 33/6839* (2013.01); *G01N 21/77* (2013.01); *G01N 2021/7759* (2013.01); *G01N 21/78* (2013.01); *G01N 2333/765* (2013.01)

(58) Field of Classification Search
CPC ......... G01N 33/6839; G01N 2333/765; G01N 2021/7759
See application file for complete search history.

(56) References Cited

U.S. PATENT DOCUMENTS 5,013,527 A * 5/1991 Arai ..................... G01N 33/526
422/423

FOREIGN PATENT DOCUMENTS

| EP | 0769697 A1 * | 4/1997 | ....... G01N 33/54366 |
|---|---|---|---|
| JP | H10-232233 A | 9/1998 | |
| JP | 2004-333452 A | 11/2004 | |
| JP | 2018-025486 A | 2/2018 | |

OTHER PUBLICATIONS

The extended European search report issued by the European Patent Office on Mar. 30, 2022, which corresponds to European Patent Application No. 21210873.2—1111 and is related to U.S. Appl. No. 17/535,925.

* cited by examiner

*Primary Examiner* — Jennifer Wecker
*Assistant Examiner* — Michelle Adams
(74) *Attorney, Agent, or Firm* — Studebaker & Brackett PC

(57) ABSTRACT

A dry test piece for albumin measurement is based on the improved BCP method as a principle, and enables the measurement of albumin at a high sensitivity. The test piece includes a support; and a reagent holding layer provided on the support and on which a sample is spotted. The reagent holding layer contains a protein denaturation agent (component A), an SH reagent (component B), bromcresol purple (component C), and a nonionic surfactant (component D). In the reagent holding layer, a weight ratio (D/C) of the component D to the component C is 0.3 to 13, a content of the component C relative to an amount of the spotted sample is 0.4 μg/μL to 5.4 μg/μL, a content of the component D relative to the amount of the spotted sample is 25 μg/μL or less.

22 Claims, 9 Drawing Sheets

FIG. 7

| Emulgen420 [ug/uL] | 0.01 | 0.3 | 0.5 | 1.1 | 1.6 | 2.2 | 2.7 | 3.2 | 3.8 | 4.3 | 4.9 | 5.4 |
|---|---|---|---|---|---|---|---|---|---|---|---|---|
| 30.0 | | | | | | ○13.9 | | | | | | |
| 25.0 | | | | | | | | | | | | |
| 23.0 | | | | | | | | | | | | |
| 20.0 | | | | | | | | | | | | |
| 18.8 | | | | | | | | | | | | |
| 15.0 | | | | | | | | | | | | |
| 12.5 | | | | | | | | | | | | ◎2.3 |
| 11.3 | | | | | | | | | | | | |
| 10.0 | | | | | | ◎4.6 | | | | ◎2.3 | | |
| 8.8 | | | | | | | | | | | | |
| 7.5 | | | | | | | | | | | | |
| 6.3 | | | | | | | | | | | | |
| 5.0 | ×462.8 | ○18.5 | ◎9.3 | | | ◎2.3 | | ◎1.5 | | ◎1.2 | | ◎0.9 |
| 3.8 | | | | | | ◎1.7 | | | | | | |
| 2.5 | | | | | | | | | | | | |
| 1.3 | | | ◎2.3 | | | | | | | | | |
| 0.6 | | ○2.3 | | | | ○0.3 | | | | | | |
| 0.03 | ×2.3 | | | | | | | | | | | |

BCP Concentration [ug/uL]

FIG. 8

| Emulgen420 [ug/cm²] | 0.2 | 3.9 | 7.7 | 15.4 | 23.2 | 30.9 | 38.6 | 46.3 | 54.0 | 61.7 | 69.5 | 77.2 |
|---|---|---|---|---|---|---|---|---|---|---|---|---|
| 428.6 | | | | | | ○13.9 | | | | | | |
| 357.1 | | | | | | | | | | | | |
| 328.6 | | | | | | | | | | | | |
| 285.7 | | | | | | | | | | | | |
| 267.9 | | | | | | | | | | | | |
| 214.3 | | | | | | | | | | | | |
| 178.6 | | | | | | | | | | | | ◎2.3 |
| 160.7 | | | | | | | | | | | | |
| 142.9 | | | | | | ◎4.6 | | | | ◎2.3 | | |
| 125.0 | | | | | | | | | | | | |
| 107.1 | | | | | | | | | | | | |
| 89.3 | | | | | | | | | | | | |
| 71.4 | ×462.8 | ○18.5 | ◎9.3 | | | ◎2.3 | | ◎1.5 | | ◎1.2 | | ◎0.9 |
| 53.6 | | | | | | ◎1.7 | | | | | | |
| 35.7 | | | | | | | | | | | | |
| 17.9 | | | ◎2.3 | | | | | | | | | |
| 8.9 | | ○2.3 | | | | ○0.3 | | | | | | |
| 0.4 | ×2.3 | | | | | | | | | | | |

BCP Concentration [ug/cm²]

FIG. 11

| Tween20 [ug/uL] | 0.01 | 0.3 | 0.5 | 1.1 | 1.6 | 2.2 | 2.7 | 3.2 | 3.8 | 4.3 | 4.9 | 5.4 |
|---|---|---|---|---|---|---|---|---|---|---|---|---|
| 30.0 | | | | | | ○13.9 | | | | | | |
| 25.0 | | | | | | | | | | | | |
| 23.0 | | | | | | ○10.6 | | | | | | |
| 20.0 | | | | | | | | | | | | |
| 18.8 | | | | | | | | | | | | |
| 15.0 | | | | | | | | | | | | |
| 12.5 | | | | | | | | | | | | ○2.3 |
| 11.3 | | | | | | | | | | | | |
| 10.0 | | | | | | | | | | ◉2.3 | | |
| 8.8 | | | | | | | | | | | | |
| 7.5 | | | | | | | | | | | | |
| 6.3 | | | | | | | | | | | | |
| 5.0 | ×462.8 | ○18.5 | | | | | | | | ○1.2 | | ○0.9 |
| 3.8 | | | | | | ◉1.7 | | | | | | |
| 2.5 | | | | | | ○1.2 | | | | | | |
| 1.3 | | | | | | | | | | | | |
| 0.6 | | ○2.3 | | | | ○0.3 | | | | | | |
| 0.03 | ×2.3 | | | | | | | | | | | |

BCP Concentration [ug/uL]

FIG. 12

| Tween20 [ug/cm²] | 0.2 | 3.9 | 7.7 | 15.4 | 23.2 | 30.9 | 38.6 | 46.3 | 54.0 | 61.7 | 69.5 | 77.2 |
|---|---|---|---|---|---|---|---|---|---|---|---|---|
| 428.6 | | | | | | ○13.9 | | | | | | |
| 357.1 | | | | | | | | | | | | |
| 328.6 | | | | | | ○10.6 | | | | | | |
| 285.7 | | | | | | | | | | | | |
| 267.9 | | | | | | | | | | | | |
| 214.3 | | | | | | | | | | | | |
| 178.6 | | | | | | | | | | | | ○2.3 |
| 160.7 | | | | | | | | | | | | |
| 142.9 | | | | | | | | | | ◉2.3 | | |
| 125.0 | | | | | | | | | | | | |
| 107.1 | | | | | | | | | | | | |
| 89.3 | | | | | | | | | | | | |
| 71.4 | ×462.8 | ○18.5 | | | | | | | | ○1.2 | | ○0.9 |
| 53.6 | | | | | | ◉1.7 | | | | | | |
| 35.7 | | | | | | ○1.2 | | | | | | |
| 17.9 | | | | | | | | | | | | |
| 8.9 | | ○2.3 | | | | ○0.3 | | | | | | |
| 0.4 | ×2.3 | | | | | | | | | | | |

BCP Concentration [ug/cm²]

| Tween80 [ug/uL] | 0.01 | 0.3 | 0.5 | 1.1 | 1.6 | 2.2 | 2.7 | 3.2 | 3.8 | 4.3 | 4.9 | 5.4 |
|---|---|---|---|---|---|---|---|---|---|---|---|---|
| 30.0 | | | | | | ◎13.9 | | | | | | |
| 25.0 | | | | | | | | | | | | |
| 23.0 | | | | | | ◎10.6 | | | | | | |
| 20.0 | | | | | | | | | | | | |
| 18.8 | | | | | | | | | | | | |
| 15.0 | | | | | | | | | | | | |
| 12.5 | | | | | | | | | | | | ◎2.3 |
| 11.3 | | | | | | | | | | | | |
| 10.0 | | | ◎9.3 | | | ◎4.6 | | | ◎2.3 | | | |
| 8.8 | | | | | | | | | | | | |
| 7.5 | | | | | | | | | | | | |
| 6.3 | | | | | | | | | | | | |
| 5.0 | ×462.8 | ○18.5 | ◎9.3 | | | ◎2.3 | | ◎1.5 | | | | ○0.9 |
| 3.8 | | | | | | ◎1.7 | | | | | | |
| 2.5 | | | | | | ◎1.2 | | | | | | |
| 1.3 | | | | | | | | | | | | |
| 0.6 | | ○2.3 | | | | ○0.3 | | | | | | |
| 0.03 | ×2.3 | | | | | | | | | | | |

BCP Concentration [ug/uL]

FIG. 16

| Tween80 [ug/cm²] | 0.2 | 3.9 | 7.7 | 15.4 | 23.2 | 30.9 | 38.6 | 46.3 | 54.0 | 61.7 | 69.5 | 77.2 |
|---|---|---|---|---|---|---|---|---|---|---|---|---|
| 428.6 | | | | | | ◎13.9 | | | | | | |
| 357.1 | | | | | | | | | | | | |
| 328.6 | | | | | | ◎10.6 | | | | | | |
| 285.7 | | | | | | | | | | | | |
| 267.9 | | | | | | | | | | | | |
| 214.3 | | | | | | | | | | | | |
| 178.6 | | | | | | | | | | | | ◎2.3 |
| 160.7 | | | | | | | | | | | | |
| 142.9 | | | ◎9.3 | | | ◎4.6 | | | ◎2.3 | | | |
| 125.0 | | | | | | | | | | | | |
| 107.1 | | | | | | | | | | | | |
| 89.3 | | | | | | | | | | | | |
| 71.4 | ×462.8 | ○18.5 | ◎9.3 | | | ◎2.3 | | ◎1.5 | | | | ○0.9 |
| 53.6 | | | | | | ◎1.7 | | | | | | |
| 35.7 | | | | | | ◎1.2 | | | | | | |
| 17.9 | | | | | | | | | | | | |
| 8.9 | | ○2.3 | | | | ○0.3 | | | | | | |
| 0.4 | ×2.3 | | | | | | | | | | | |

BCP Concentration [ug/cm²]

TEST PIECE FOR ALBUMIN MEASUREMENT

BACKGROUND

1. Field

The present disclosure relates to a test piece for albumin measurement, and particularly relates to a test piece used for albumin measurement using the improved bromocresol purple (BCP) method, and a method for measuring albumin using the test piece for albumin measurement.

2. Description of Related Art

Known methods for measuring albumin in a biological specimen include the immunoassay method of measuring a scattering intensity derived from an antigen-antibody complex using an anti-albumin serum, and the dye binding method in which a dye such as bromocresol green (BCG) or BCP is used, and the dye binding method is widely used in routine laboratory tests. In recent years, the improved BCP method is particularly used as a method having high correlations with immunoassay method (JP-A-10(1998)-232233). In the improved BCP method, a protein denaturation agent and a sulfhydryl reagent (SH reagent) are used to change reduced albumin to oxidized albumin, and thereafter, oxidized albumin is caused to react with BCP.

SUMMARY

The improved BCP method has high specificity to albumin and is generally used as described above, and an albumin measurement reagent of a liquid type is mainly used, which is a solution containing BCP, a protein denaturation agent, and an SH reagent (liquid reagent) to be mixed with a biological specimen so that albumin and BCP are caused to react. There has been no dry-type albumin measurement reagent containing BCP, a protein denaturation agent, and an SH reagent to be directly mixed with a biological specimen so that albumin and BCP are caused to react. There has been no test piece for albumin measurement based on the improved BCP method, i.e., a test piece for albumin measurement containing BCP, a protein denaturation agent and an SH reagent.

The present disclosure provides a test piece for albumin measurement that enables the measurement of albumin at a high sensitivity based on the improved BCP method as a principle, and provides a test piece for albumin measurement that enables the measurement of albumin at a high accuracy.

The present disclosure, in one aspect, relates to a test piece for albumin measurement for measuring albumin contained in a sample, the test piece for albumin measurement comprising a support and a reagent holding layer provided on the support and on which the sample is spotted, wherein the reagent holding layer contains a protein denaturation agent (component A), an SH reagent (component B), BCP (component C), and a nonionic surfactant (component D). In the reagent holding layer, a weight ratio (D/C) of the component D to the component C is 0.3 to 13, a content of the component C relative to the amount of the spotted sample is 0.4 µg/µL to 5.4 µg/µL, and a content of the component D relative to the amount of the spotted sample is 25 µg/µL or less.

The present disclosure, in another aspect, relates to a test piece for albumin measurement for measuring albumin contained in a sample, the test piece for albumin measurement comprising a support and a reagent holding layer that is provided on the support and on which the sample is spotted, wherein the reagent holding layer contains a protein denaturation agent (component A), an SH reagent (component B), BCP (component C), and polyoxyethylene (23) lauryl ether (component D). In the reagent holding layer, a weight ratio (D/C) of a component D to the component C is 1.3 to 13, a content of the component C relative to the amount of the spotted sample is 0.4 µg/µL to 5 µg/µL, and a content of the component D relative to the amount of the spotted sample is 20 µg/µL or less.

The present disclosure, in another aspect, relates to a method for measuring an amount of albumin based on measured values of optical properties of BCP under the presence of a protein denaturation agent and an SH reagent, the method comprising spotting a predetermined amount of a sample on a reagent holding layer of a test piece, the reagent holding layer containing a protein denaturation agent (component A), an SH reagent (component B), BCP (component C), and a nonionic surfactant (component D), so that a mixture solution in which the sample and the components A, B, C, and D are mixed is prepared. In the mixture solution, a weight ratio (D/C) of the component D to the component C is 0.3 to 13, a concentration of the component C is 0.4 µg/µL to 5.4 µg/µL, and a concentration of the component D is 25 µg/µL or less.

The present disclosure, in another aspect, relates to a method for measuring an amount of albumin based on measured values of optical properties of BCP under the presence of a protein denaturation agent and an SH reagent, the method comprising spotting a predetermined amount of a sample on a reagent holding layer of a test piece, the reagent holding layer containing a protein denaturation agent (component A), an SH reagent (component B), BCP (component C), and polyoxyethylene (23) lauryl ether (component D), so that a mixture solution in which the sample and the components A, B, C, and D are mixed is prepared. In the mixture solution, a weight ratio (D/C) of the component D to the component C is 1.3 to 13, a concentration of the component C is 0.4 µg/µL to 5 µg/µL, and a concentration of the component D is 20 µg/µL or less.

With the present disclosure, it is possible to provide a test piece for albumin measurement that enables the measurement of albumin at a high sensitivity based on the improved BCP method as a principle, and provides a test piece for albumin measurement that enables the measurement of albumin at a high accuracy.

BRIEF DESCRIPTION OF THE DRAWINGS

FIG. 1A is a perspective view, and FIG. 1B is a longitudinal cross-sectional view taken along line A-A.

FIG. 7 shows each ratio (D/C) between the content of BCP (component C) and the content of polyoxyethylene (13) oleyl ether (Emulgen 420) (component D) relative to the amount of a spotted sample in a test piece for albumin measurement based on Example, and evaluation thereof.

FIG. 8 shows each ratio (D/C) between the content of BCP (component C) and the content of polyoxyethylene (13) oleyl ether (Emulgen 420) (component D) per unit area of a sample spot surface (surface on which a sample is spotted) of a reagent holding layer in a test piece for albumin measurement based on Example, and evaluation thereof.

FIG. 11 shows each ratio (D/C) between the content of BCP (component C) and the content of polyoxyethylene (20) sorbitan monolaurate (Tween 20) (component D) relative to the amount of a spotted sample in a test piece for albumin measurement based on Example, and evaluation thereof.

FIG. 12 shows each ratio (D/C) between the content of BCP (component C) and the content of polyoxyethylene (20) sorbitan monolaurate (Tween 20) (component D) per unit area of a sample spot surface (surface on which a sample is spotted) of a reagent holding layer in a test piece for albumin measurement based on Example, and evaluation thereof.

FIG. 13 shows each ratio (D/C) between the content of BCP (component C) and the content of polyoxyethylene (12) lauryl ether (Emulgen 120) (component D) relative to the amount of a spotted sample in a test piece for albumin measurement based on Example, and evaluation thereof.

FIG. 14 shows each ratio (D/C) between the content of BCP (component C) and the content of polyoxyethylene (12) lauryl ether (Emulgen 120) (component D) per unit area of a sample spot surface (surface on which a sample is spotted) of a reagent holding layer in a test piece for albumin measurement based on Example, and evaluation thereof.

FIG. 15 shows each ratio (D/C) between the content of BCP (component C) and the content of polyoxyethylene (20) sorbitan monooleate (Tween 80) (component D) in the amount of a spotted sample in a test piece for albumin measurement based on Example, and evaluation thereof.

FIG. 16 shows each ratio (D/C) between the content of BCP (component C) and the content of polyoxyethylene (20) sorbitan monooleate (Tween 80) (component D) per unit area of a sample spot surface (surface on which a sample is spotted) of a reagent holding layer in a test piece for albumin measurement based on Example, and evaluation thereof.

DETAILED DESCRIPTION

Figure 1A:
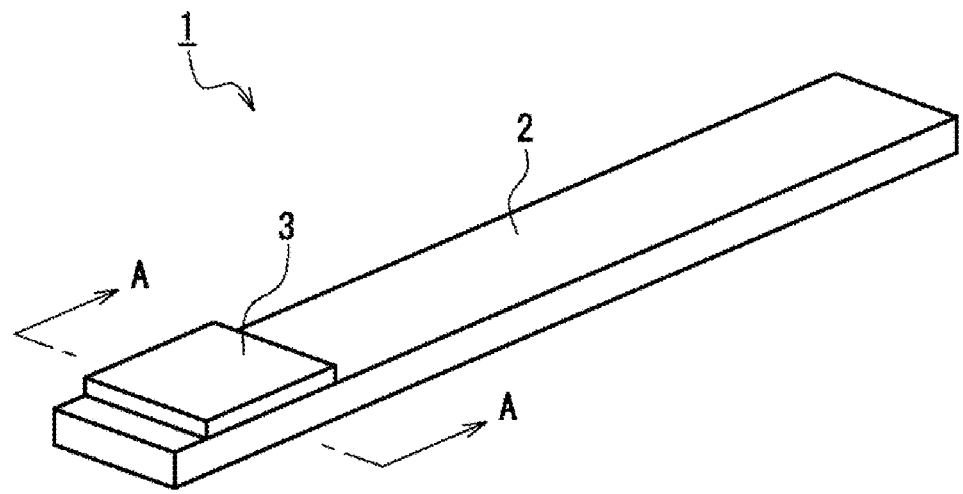
FIGS. 1A and 1B illustrate a configuration of a test piece for albumin measurement according to Embodiment 1 of the present disclosure.

The improved BCP method is a method in which reduced albumin in a sample is oxidized under the presence of a protein denaturation agent and an SH reagent so that the reduced albumin changes into oxidized albumin, and the oxidized albumin is allowed to bind with BCP, whereby an optical property of BCP, for example, the absorbance thereof changes, and the change is measured. Specifically, an absorbance at a wavelength of 570 to 660 nm is measured. In a case of a dry-type measurement with respect to a test piece or the like, a dry reagent is dissolved in a liquid sample, and therefore, characteristics of the sample itself, or optical properties thereof significantly influence the measurement results. Particularly when the sample is serum or plasma, it contains hemoglobin eluted from erythrocytes due to hemolysis in some cases. Hemoglobin absorbs light at wavelengths in the vicinity of 610 nm, and the measurement wavelength of the improved BCP method is also in the vicinity of 610 nm. Therefore, the presence of hemoglobin greatly influences the measurement of albumin. Correction or calibration to remove influences of hemoglobin may be considered to cope with this, but in the case of dry-type measurement, it is very difficult and complicated to perform correction or calibration, as compared with a liquid-type measurement.

The present disclosure is based on the following findings: With a configuration in which a nonionic surfactant (for example, polyoxyethylene (23) lauryl ether) (component D), in addition to a protein denaturation agent (component A), an SH reagent (component B), and BCP (component C), which are commonly used in a liquid-type measurement using the improved BCP method, is contained in a reagent holding layer, and the ratio (D/C, weight ratio) of the nonionic surfactant such as polyoxyethylene (23) lauryl ether (component D) with respect to BCP (component C) in the reagent holding layer, and the contents of these components, are set in predetermined ranges, it is possible to measure albumin at a high sensitivity. It is also possible to measure albumin at a high accuracy while suppressing influences of a co-existing substance such as hemoglobin in serum. The numerical value in the brackets of "polyoxyethylene (23) lauryl ether" indicates the number of added moles of an oxyethylene group.

With the present disclosure, it is possible to provide a dry test piece for albumin measurement based on the improved BCP method as a principle. With the present disclosure, it is possible to provide a dry test piece for albumin measurement that is based on the improved BCP method as a principle and enables the measurement of albumin at a high sensitivity. With the present disclosure, it is possible to measure albumin in a sample at a high accuracy even in a case where hemoglobin is contained in the sample.

[Test Piece for Albumin Measurement]

The test piece for albumin measurement of the present disclosure comprises a support and a reagent holding layer provided on the support, and is intended to measure albumin based on the improved BCP method. In one embodiment, the reagent holding layer contains a protein denaturation agent (component A), an SH reagent (component B), BCP (component C), and a nonionic surfactant (component D), a weight ratio (D/C) of the component D to the component C is 0.3 to 13, a content of the component C relative to the amount of the sample spotted on the reagent holding layer is 0.4 µg/µL to 5.4 µg/µL, and a content of the component D relative to the amount of the sample spotted on the reagent holding layer is 25 µg/µL or less.

The reagent holding layer is a part that contains a reagent used for the measurement of albumin and on which a sample is spotted, and in some of embodiments, the reagent holding layer is formed with a porous substance or the like, as is described below. When a predetermined amount of a sample is spotted on the reagent holding layer, in some of embodiments, the sample spreads over an entirety of the reagent holding layer and is held in the reagent holding layer, whereby the entirety of the reagent holding layer is immersed in the sample. This predetermined amount of the sample spotted can be considered as a sample holding capacity of the reagent holding layer. The amount of the sample spotted is substantially identical to the sample holding capacity of the reagent holding layer. The predetermined amount of the sample (the amount of the sample spotted) can be determined appropriately, and in some embodiments, it is about 1 to 20 µL.

In some embodiments of the present disclosure, the "reagent holding layer" in the test piece of the present disclosure contains a reagent in a dry state (dry reagent). The dry reagent may contain a protein denaturation agent (component A), an SH reagent (component B), BCP (component C), and a nonionic surfactant (component D), in a dry state. "Dry" of "dry reagent" in the present disclosure implies containing substantially no water, and refers to a reagent in a solid state.

[Component C]

As BCP (component C) a commercially available source can be used. BCP is also referred to as bromocresol purple or bromcresol purple. The chemical name of BCP is 5,5'-dibromo-o-cresol sulfonephthalein (CAS No. 115-40-2).

The ratio (D/C, weight ratio) of the component D to the component C in the reagent holding layer is 0.3 to 13. From the viewpoint of enabling the measurement at a high accuracy while suppressing influences of hemoglobin in a sample, the ratio is preferably 1.3 to 13.

In some embodiments, the content of the component C relative to the amount of the spotted sample in the reagent holding layer is 0.4 µg/µL to 5.4 µg/µL. From the viewpoint of enabling the measurement at a high accuracy while suppressing influences of hemoglobin in a sample, the content is preferably 0.4 µg/µL to 5 µg/µL.

In some embodiments, the content of the component C in the reagent holding layer is 5.8 µg/cm$^2$ to 77.2 µg/cm$^2$. From the viewpoint of enabling the measurement at a high accuracy while suppressing influences of hemoglobin in a sample, the content is preferably 5.8 µg/cm$^2$ to 71.5 µg/cm$^2$. The "content" (µg/cm$^2$) in the reagent holding layer in the present disclosure refers to a content per unit area of the sample spot surface (surface on which a sample is spotted) in the reagent holding layer.

[Component D]

The nonionic surfactant in some embodiments of the present disclosure is a nonionic surfactant having a polyoxyethylene group. The nonionic surfactant including a polyoxyethylene group may include polyoxyethylene alkyl ether, polyoxyethylene distyrenated phenyl ether, polyoxyethylene polyoxypropylene alkyl ether, or aliphatic acid ester. Polyoxyethylene alkyl ether may include polyoxyethylene lauryl ether, polyoxyethylene cetyl ether, polyoxyethylene stearyl ether, polyoxyethylene oleyl ether, or polyoxyethylene myristyl ether. Aliphatic acid ester may include polyoxyethylene sorbitan monolaurate, or polyoxyethylene sorbitan monooleate.

The nonionic surfactant may include polyoxyethylene (23) lauryl ether, polyoxyethylene distyrenated phenyl ether, polyoxyethylene (13) oleyl ether, polyoxyethylene polyoxypropylene alkyl ether, polyoxyethylene (20) sorbitan monolaurate, polyoxyethylene (12) lauryl ether, or polyoxyethylene (20) sorbitan monooleate.

In some embodiments, one type of the nonionic surfactant may be used, or a plurality of types of the nonionic surfactants may be used.

The average number of added moles of the ethyleneoxy group of the nonionic surfactant in the present disclosure is, for example, 10, 11, 12, 13, or more, and 25, 24, 23, or less.

The nonionic surfactant in the present disclosure may have an HLB of 13 to 17, or 13.4 to 16.9. The "HLB" in the present disclosure refers to a griffin HLB value. The griffin HLB value is defined in J. Soc. Cosm. Chem. 1954 (vol. 5), pp. 249 to 256.

In some embodiments, the content of the component D relative to the amount of the spotted sample in the reagent holding layer may be 25 µg/µL or less. From the viewpoint of enabling the measurement at a high accuracy while suppressing influences of hemoglobin in a sample, the content is preferably 20 µg/µL or less.

In some embodiments, the content of the component D in the reagent holding layer may be 357 µg/cm$^2$ or less. From the viewpoint of enabling the measurement at a high accuracy while suppressing influences of hemoglobin in a sample, the content is preferably 300 µg/cm$^2$ or less.

The protein denaturation agent (component A), the SH reagent (component B), and BCP (component C) contained in the reagent holding layer of the test piece of the present disclosure are components that are considered essential in the measurement of albumin using the improved BCP method as a principle.

[Component A]

The protein denaturation agent (component A) may be an anionic surfactant, an amphoteric-ionic surfactant, urea, a guanidine salt, an inorganic salt, or a thiocyanic acid salt. In some embodiments, one component A may be used alone, or two or more components A may be used in combination. The protein denaturation agent (component A), in some embodiments, contains substantially no nonionic surfactant used as the component D, and preferably contains substantially no nonionic surfactant. In the present disclosure, "contains substantially no nonionic surfactant" means that the content of the nonionic surfactant in the protein denaturation agent (component A) is, in some of embodiments, 3% by mass or less, 1% by mass or less, or 0.1% by mass, and preferably 0% by mass, which means that no nonionic surfactant is contained.

In some embodiments, the guanidine salt includes guanidine hydrochloric acid salt, or guanidine sulfuric acid salt. The inorganic salt may include sodium fluoride, sodium azide, sodium chloride, or potassium chloride. The thiocyanic acid salt may include ammonium thiocyanate, potassium thiocyanate, or sodium thiocyanate.

The component A is, in some embodiments, preferably an anionic surfactant. The anionic surfactant is, in some embodiments, an alkyl sulfuric acid ester surfactant, a polyoxyethylene alkyl phenyl ether sulfuric acid ester salt, a polyoxyethylene alkyl ether sulfuric acid ester salt, or an alkylbenzene sulfonic acid salt. The alkyl sulfuric acid ester surfactant is, in some embodiments, sodium lauryl sulfate (SDS), or sodium cetyl sulfate. The polyoxyethylene alkyl phenyl ether sulfuric acid ester salt is, in some embodiments, sodium polyoxyethylene alkyl phenyl ether sulfate. The polyoxyethylene alkyl ether sulfuric acid ester salt is, in some embodiments, sodium polyoxyethylene alkyl ether sulfate, or triethanolamine polyoxyethylene alkyl ether sulfate. The alkylbenzene sulfonic acid salt is, in some embodiments, sodium lauryl benzenesulfonate, or sodium cetyl benzenesulfonate.

The component A is, in some embodiments, preferably SDS, or sodium lauryl benzenesulfonate.

In some embodiments, the content of the component A relative to the amount of the spotted sample in the reagent holding layer is 0.1 μg/μL to 15 μg/μL. From the viewpoint of enabling the obtainment of a higher sensitivity with respect to albumin and enabling the measurement of albumin at a higher accuracy even with respect to a sample with hemolysis, the content is more preferably 0.1 μg/μL to 5 μg/μL.

In some embodiments, the content of the component A in the reagent holding layer is 1 μg/cm$^2$ to 215 μg/cm$^2$. From the viewpoint of enabling the obtainment of a higher sensitivity with respect to albumin and enabling the measurement of albumin at a higher accuracy even with respect to a sample with hemolysis, the content is preferably 1 μg/cm$^2$ to 72 μg/cm$^2$.

[Component B]

The SH reagent (component B) is, in some embodiments, a disulfide compound, an oxidizing agent, an alkylating agent, maleimide or a derivative thereof, or thiophthalimide. In some of embodiments, one component B may be used alone, or two or more components B may be used in combination.

The disulfide compound is, in some embodiments, 5,5'-dithiobis(2-nitrobenzoic acid) (DTNB), 2,2'-dithiobis(5-nitropyridine) (NPDS), 2,2'-dithiodipyridine (2-PDS), 4,4'-dithiodipyridine (4-PDS), 4,4'-dithiobis(1-azido benzene) (DTBPA), or oxidized glutathione. The oxidizing agent includes iodine, a ferricyanide, iodosobenzoic acid, a chlorite, mercury, or zinc. The alkylating agent includes, in some embodiments, iodoacetic acid, chloroacetic acid, iodoacetamide, or chloroacetophenone. The maleimide derivative includes, in some embodiments, N-methylmaleimide, N-ethylmaleimide, or N,N'-p-phenylenedimaleimide.

The component B is, in some of embodiments, preferably a disulfide compound such as DTNB, 2-PDS, or 4-PDS, maleimide, or a maleimide derivative such as N-ethylmaleimide.

The content of the component B relative to the amount of the spotted sample in the reagent holding layer is, in some of embodiments, 0.0004 μg/μL to 8 μg/μL. From the viewpoint of enabling the obtainment of a higher sensitivity with respect to albumin and enabling the measurement of albumin at a higher accuracy even with respect to a sample with hemolysis, the content is preferably 1.5 μg/μL to 2 μg/μL.

The content of the component B in the reagent holding layer is, in some of embodiments, 0.01 μg/cm$^2$ to 115 μg/cm$^2$. From the viewpoint of enabling the obtainment of a higher sensitivity with respect to albumin and enabling the measurement of albumin at a higher accuracy even with respect to a sample with hemolysis, the content is preferably 20 μg/cm$^2$ to 30 μg/cm$^2$.

The reagent holding layer, in some of embodiments, may contain a buffer and/or a preservative additionally.

The buffer includes, in some of embodiments, an acetic acid salt, a citric acid salt, a phosphoric acid salt, a succinic acid salt, a malic acid salt, or Good's buffer. The Good's buffer includes, in some of embodiments, 3-(N-morpholino) ethanesulfonic acid (MES), or Bis-Tris. The buffer is preferably a citric acid salt, a malic acid salt, a succinic acid salt, or 3-(N-morpholino)ethanesulfonic acid (MES). The buffer, in some of embodiments, has a pKa of 4.5 to 6.0, and preferably 5.0 to 5.5. From the viewpoint of obtaining sufficient color development of BCP when a sample containing albumin is measured, and suppressing the color development of BCP when a sample containing no albumin is measured, the buffer is contained in the reagent holding layer in such a manner that a reaction solution after a sample spotted on the reagent holding layer (a mixture solution of the sample and the reagents) has a pH of 4.5 to 6.0, and preferably 5.0 to 5.5.

The reagent holding layer, in some of embodiments, may be formed by impregnating a reagent holding member with a reagent solution containing the above-described reagent (the components A, B, C, and D, and the like) and drying the same, or alternatively, directly providing a reagent solution on a support and drying the same. The reagent holding member is not limited to a specific member, as long as it is a member that can hold a reagent used in the measurement of albumin. A specimen (sample) spotted on the reagent holding layer spreads throughout the reagent holding layer and is mixed with the reagent. In some of embodiments, a porous substance, a fibrous substance, or the like can be used for forming the reagent holding member. In some of embodiments, the reagent holding member may be in a sheet form or in a membrane form. The reagent holding member is, in some of embodiments, a member in a paper form, a foam (foamed material), a member in a woven fabric form, a member in a non-woven fabric form, or a member in a knitted fabric form. The material for forming the reagent holding member includes, in some of embodiments, cotton, hemp, cellulose, nitrocellulose, cellulose acetate, rock wool, glass fiber, silica fiber, carbon fiber, boron fiber, polyamide, aramid, polyvinyl alcohol, polyvinyl acetate, rayon, polyester, nylon, polyacrylic acid, polyacrylic acid ester, or polyolefin. The shape of the reagent holding layer is not limited particularly, and in some of embodiments, the shape thereof is a square, a rectangle, or a circle.

The support is, in some of embodiments, preferably formed with a liquid-impermeable material. The material of the support includes, in some of embodiments, paper, plastic (synthetic resin), or a metal.

One embodiment of the test piece of the present disclosure is described below.

[Component D: Polyoxyethylene (23) Lauryl Ether]

The test piece of the present disclosure, in one aspect, contains polyoxyethylene (23) lauryl ether as the component D. As polyoxyethylene (23) lauryl ether, in some of embodiments, Brij (registered trademark) 35 (product name: Polyoxyethylene 23 Lauryl Ether, molecular weight: 1225) can be used.

In the present aspect, from the viewpoint of enabling the measurement at a high accuracy while suppressing influences of hemoglobin in a sample, the ratio (D/C, weight ratio) of the component D to the component C in the reagent holding layer is preferably 1.3 to 13, and from the viewpoint of enabling the measurement at a higher accuracy while further suppressing influences of hemoglobin in a sample, the ratio is preferably 1.5 to 9.3. From the viewpoint of enabling the obtainment of a higher sensitivity with respect to albumin and enabling the measurement of albumin at a higher accuracy even with respect to a sample with hemolysis, the ratio is more preferably 1.5 to 2.9.

In the present aspect, from the viewpoint of enabling the measurement at a high accuracy while suppressing influences of hemoglobin in a sample, the content of the component C relative to the amount of the spotted sample in the reagent holding layer is preferably 0.4 µg/µL to 5 µg/µL, and from the viewpoint of enabling the measurement at a higher accuracy while further suppressing influences of hemoglobin in a sample, the content is preferably 0.5 µg/µL to 4.3 µg/µL. From the viewpoint of enabling the obtainment of a higher sensitivity with respect to albumin and enabling the measurement of albumin at a higher accuracy even with respect to a sample with hemolysis, the content is more preferably 1.6 µg/µL to 3.8 µg/µL.

In the present aspect, from the viewpoint of enabling the measurement at a high accuracy while suppressing influences of hemoglobin in a sample, the content of the component D relative to the amount of the spotted sample in the reagent holding layer is preferably 20 µg/µL or less, and from the viewpoint of enabling the measurement at a higher accuracy while further suppressing influences of hemoglobin in a sample, the content is preferably 1.3 µg/µL to 20 µg/µL. From the viewpoint of enabling the obtainment of a higher sensitivity with respect to albumin and enabling the measurement of albumin at a higher accuracy even with respect to a sample with hemolysis, the content is more preferably 3.8 µg/µL to 8.8 µg/µL.

[Component D: Polyoxyethylene Distyrenated Phenyl Ether]

The test piece of the present disclosure, in one aspect, contains polyoxyethylene distyrenated phenyl ether as the component D. As polyoxyethylene distyrenated phenyl ether, in some of embodiments, Emulgen A90 (produced by Kao Corporation, HLB: 14.5) can be used.

In the present aspect, from the viewpoint of enabling the measurement at a higher accuracy while further suppressing influences of hemoglobin in a sample, the ratio (D/C, weight ratio) of the component D to the component C in the reagent holding layer is preferably 1.2 to 10.6. From the viewpoint of enabling the obtainment of a higher sensitivity with respect to albumin and enabling the measurement of albumin at a higher accuracy even with respect to a sample with hemolysis, the ratio is more preferably 1.2 to 2.3.

In the present aspect, from the viewpoint of enabling the measurement at a higher accuracy while further suppressing influences of hemoglobin in a sample, the content of the component C relative to the amount of the spotted sample in the reagent holding layer is preferably 0.5 µg/µL to 5.4 µg/µL. From the viewpoint of enabling the obtainment of a higher sensitivity with respect to albumin and enabling the measurement of albumin at a higher accuracy even with respect to a sample with hemolysis, the content is more preferably 2.2 µg/µL to 5.4 µg/µL.

In the present aspect, from the viewpoint of enabling the measurement at a higher accuracy while further suppressing influences of hemoglobin in a sample, the content of the component D relative to the amount of the spotted sample in the reagent holding layer is preferably 23.0 µg/µL or less. From the viewpoint of enabling the obtainment of a higher sensitivity with respect to albumin and enabling the measurement of albumin at a higher accuracy even with respect to a sample with hemolysis, the content is more preferably 12.5 µg/µL or less, and further preferably 3.8 µg/µL to 12.5 µg/µL.

[Component D: Polyoxyethylene (13) Oleyl Ether]

The test piece of the present disclosure, in one aspect, contains polyoxyethylene (13) oleyl ether as the component D. As polyoxyethylene (13) oleyl ether, in some of embodiments, Emulgen 420 (produced by Kao Corporation, HLB: 13.6) can be used.

In the present aspect, from the viewpoint of enabling the measurement at a higher accuracy while further suppressing influences of hemoglobin in a sample, the ratio (D/C, weight ratio) of the component D to the component C in the reagent holding layer is preferably 0.9 to 9.3. From the viewpoint of enabling the obtainment of a higher sensitivity with respect to albumin, the ratio is more preferably 0.9 to 2.3.

In the present aspect, from the viewpoint of enabling the measurement at a higher accuracy while further suppressing influences of hemoglobin in a sample, the content of the component C relative to the amount of the spotted sample in the reagent holding layer is preferably 0.5 µg/µL to 5.4 µg/µL. From the viewpoint of enabling the obtainment of a higher sensitivity, the content is more preferably 2.2 µg/µL to 5.4 µg/µL.

In the present aspect, from the viewpoint of enabling the measurement at a higher accuracy while further suppressing influences of hemoglobin in a sample, the content of the component D relative to the amount of the spotted sample in the reagent holding layer is preferably 12.5 µg/µL or less. From the viewpoint of enabling the obtainment of a higher sensitivity with respect to albumin and enabling the measurement of albumin at a higher accuracy even with respect to a sample with hemolysis, the content is more preferably 3.8 µg/µL to 12.5 µg/µL.

[Component D: Polyoxyethylene Polyoxypropylene Alkyl Ether]

The test piece of the present disclosure, in one aspect, contains polyoxyethylene polyoxypropylene alkyl ether as the component D. As polyoxyethylene polyoxypropylene alkyl ether, in some of embodiments, Emulgen LS110 (produced by Kao Corporation, HLB: 13.4) can be used.

In the present aspect, from the viewpoint of enabling the measurement at a higher accuracy while further suppressing influences of hemoglobin in a sample, the ratio (D/C, weight ratio) of the component D to the component C in the reagent holding layer is preferably 1.2 to 2.3.

In the present aspect, from the viewpoint of enabling the measurement at a higher accuracy while further suppressing influences of hemoglobin in a sample, the content of the component C relative to the amount of the spotted sample in the reagent holding layer is preferably 2.2 µg/µL to 5.4 µg/µL.

In the present aspect, from the viewpoint of enabling the measurement at a higher accuracy while further suppressing influences of hemoglobin in a sample, the content of the component D relative to the amount of the spotted sample in the reagent holding layer is preferably 12.5 µg/µL or less, and more preferably 3.8 µg/µL to 12.5 µg/µL.

[Component D: Polyoxyethylene (20) Sorbitan Monolaurate]

The test piece of the present disclosure, in one aspect, contains polyoxyethylene (20) sorbitan monolaurate as the component D. As polyoxyethylene (20) sorbitan monolaurate, in some of embodiments, Tween 20 (HLB: 16.7) can be used.

In the present aspect, from the viewpoint of enabling the measurement at a higher accuracy while further suppressing influences of hemoglobin in a sample, the ratio (D/C, weight ratio) of the component D to the component C in the reagent holding layer is preferably 1.7 to 2.3.

In the present aspect, from the viewpoint of enabling the measurement at a higher accuracy while further suppressing influences of hemoglobin in a sample, the content of the component C relative to the amount of the spotted sample in the reagent holding layer is preferably 2.2 µg/µL to 4.3 µg/µL.

In the present aspect, from the viewpoint of enabling the measurement at a higher accuracy while further suppressing influences of hemoglobin in a sample, the content of the component D relative to the amount of the spotted sample in the reagent holding layer is preferably 10.0 µg/µL or less, and more preferably 3.8 µg/µL to 10.0 µg/µL.

[Component D: Polyoxyethylene (12) Lauryl Ether]

The test piece of the present disclosure, in one aspect, contains polyoxyethylene (12) lauryl ether as the component D. As polyoxyethylene (12) lauryl ether, in some of embodiments, Emulgen 120 (produced by Kao Corporation, HLB: 15.3) can be used.

In the present aspect, from the viewpoint of enabling the measurement at a higher accuracy while further suppressing influences of hemoglobin in a sample, the ratio (D/C, weight ratio) of the component D to the component C in the reagent holding layer is preferably 1.2 to 2.3. From the viewpoint of enabling the obtainment of a higher sensitivity with respect to albumin and enabling the measurement of albumin at a higher accuracy even with respect to a sample with hemolysis, the ratio is more preferably 1.2 to 1.4.

In the present aspect, from the viewpoint of enabling the measurement at a higher accuracy while further suppressing influences of hemoglobin in a sample, the content of the component C relative to the amount of the spotted sample in the reagent holding layer is preferably 2.2 µg/µL to 4.3 µg/µL. From the viewpoint of enabling the obtainment of a higher sensitivity with respect to albumin and enabling the measurement of albumin at a higher accuracy even with respect to a sample with hemolysis, the content is more preferably 2.2 µg/µL to 3.1 µg/µL.

In the present aspect, from the viewpoint of enabling the measurement at a higher accuracy while further suppressing influences of hemoglobin in a sample, the content of the component D relative to the amount of the spotted sample in the reagent holding layer is preferably 5.0 µg/µL or less. From the viewpoint of enabling the obtainment of a higher sensitivity with respect to albumin and enabling the measurement of albumin at a higher accuracy even with respect to a sample with hemolysis, the content is more preferably 1.3 µg/µL to 3.8 µg/µL.

[Component D: Polyoxyethylene (20) Sorbitan Monooleate]

The test piece of the present disclosure, in one aspect, contains polyoxyethylene (20) sorbitan monooleate as the component D. As polyoxyethylene (20) sorbitan monooleate, in some of embodiments, Tween 80 (HLB: 15.0) can be used.

In the present aspect, from the viewpoint of enabling the measurement at a higher accuracy while further suppressing influences of hemoglobin in a sample, the ratio (D/C, weight ratio) of the component D to the component C in the reagent holding layer is preferably 1.2 to 13.9 or 1.2 to 10.6, and from the viewpoint of enabling the obtainment of a higher sensitivity with respect to albumin and enabling the measurement of albumin at a higher accuracy even with respect to a sample with hemolysis, the ratio is more preferably 1.2 to 2.3.

In the present aspect, from the viewpoint of enabling the measurement at a higher accuracy while further suppressing influences of hemoglobin in a sample, the content of the component C relative to the amount of the spotted sample in the reagent holding layer is preferably 0.5 µg/µL to 5.4 µg/µL, and from the viewpoint of enabling the obtainment of a higher sensitivity with respect to albumin and enabling the measurement of albumin at a higher accuracy even with respect to a sample with hemolysis, the content is more preferably 2.2 µg/µL to 5.4 µg/µL.

A test piece of the present disclosure, in one aspect, containing polyoxyethylene (20) sorbitan monooleate as the component D, enables the measurement of albumin at a high accuracy, even when the content of the component D relative to the amount of the spotted sample in the reagent holding layer exceeds 25 µg/µL, for example, when it is 30 µg/µL.

In the present aspect, from the viewpoint of enabling the measurement at a higher accuracy while further suppressing influences of hemoglobin in a sample, the content of the component D relative to the amount of the spotted sample in the reagent holding layer is preferably 30 µg/µL or less, 25 µg/µL or less, or 23 µg/µL or less, and from the viewpoint of enabling the obtainment of a higher sensitivity with respect to albumin and enabling the measurement of albumin at a higher accuracy even with respect to a sample with hemolysis, the content is more preferably 12.5 µg/µL or less, and further preferably 2.5 µg/µL to 12.5 µg/µL.

Therefore, in another aspect, the present disclosure relates to a test piece for measuring albumin contained in a sample, the test piece comprising a support and a reagent holding layer provided on the support and on which the sample is spotted. The reagent holding layer contains a protein denaturation agent (component A), an SH reagent (component B), BCP (component C), and a polyoxyethylene (20) sorbitan monooleate (component D), and in the reagent holding layer, a weight ratio (D/C) of the component D to the component C is 1.2 to 13.9, a content of the component C relative to the amount of the spotted sample is 0.5 µg/µL to 5.4 µg/µL, and a content of the component D relative to the amount of the spotted sample is 30 µg/µL or less.

The test piece of the present disclosure, in some of embodiments, can be used for measuring albumin in a biological specimen, and particularly enables the measurement of albumin in serum or plasma suitably even in a sample with hemolysis.

[Albumin Measuring Method]

The present disclosure, in another aspect, relates to a method for measuring an amount of albumin based on measured values of optical properties of BCP under the presence of a protein denaturation agent and an SH reagent. The measuring method of the present disclosure comprises spotting a predetermined amount of a sample on a reagent holding layer of a test piece, the reagent holding layer containing a protein denaturation agent (component A), an SH reagent (component B), BCP (component C), and a nonionic surfactant (component D), and forming a mixture solution in which the sample and the components A, B, C, and D are mixed. In the mixture solution, a ratio (D/C, weight ratio) of the component D to the component C is 0.3 to 13, a concentration of the component C is 0.4 µg/µL to 5.4 µg/µL, and a concentration of the component D is 25 µg/µL or less.

The sample in the present disclosure, in some of embodiments, is a liquid sample, for example, a biological specimen such as serum or plasma. In the measuring method of the present disclosure, in some of embodiments, when a sample (liquid) is spotted (dropped) on a reagent holding layer provided on a test piece, the sample spreads throughout the reagent holding layer, and a reagent contained in the reagent holding layer is dissolved in the sample, thereby forming a mixture solution of the sample and the reagent.

The concentration of the component C in the mixture solution, in some embodiments, is 0.4 µg/µL to 5.4 µg/µL.

In some embodiments, the concentration of the component D in the mixture solution is 25 μg/μL or less.

In some embodiments, the ratio (D/C, weight ratio) of the component D to the component C in the mixture solution is identical to that of the test piece of the present disclosure.

The concentration of the component A in the mixture solution is, in some of embodiments, 0.1 μg/μL to 15 μg/μL. From the viewpoint of enabling the obtainment of a higher sensitivity with respect to albumin and enabling the measurement of albumin at a higher accuracy even with respect to a sample with hemolysis, the content is more preferably 0.1 μg/μL to 5 μg/μL.

The concentration of the component B in the mixture solution is, in some of embodiments, 0.0004 μg/μL to 8 μg/μL. From the viewpoint of enabling the obtainment of a higher sensitivity with respect to albumin and enabling the measurement of albumin at a higher accuracy even with respect to a sample with hemolysis, the content is more preferably 1.5 μg/μL to 2 μg/μL.

The mixture solution, in some of embodiments, may additionally contain a buffer. The buffer in the mixture solution may have any concentration as long as the pH of the mixture solution can be maintained at a predetermined level. The concentration of the buffer in the mixture solution is, in some of embodiments, 300 mmol/L to 500 mmol/L. The reagent holding layer in some of embodiments preferably contains a buffer in such a manner that the reagent holding layer after the sample is spotted (the mixture solution) has a pH of 4.5 to 6.0, and preferably 5.0 to 5.5.

In the present disclosure, the concentration of each reagent in the mixture solution, when the measurement is performed with use of a test piece of the present disclosure, can be calculated by multiplying the content (μg/cm$^2$) of each reagent in a test piece (reagent holding layer) by the area (cm$^2$) of the reagent holding layer and dividing the same by an amount of a sample dropped onto the reagent holding layer. Specifically, the concentration of each reagent can be calculated by the following formula.

(Concentration of reagent)=[content (μg/cm$^2$)]×[area (cm$^2$)]÷[amount of sample (μL)]

Concentration of reagent: concentration of reagent in mixture solution content (μg/cm$^2$) of reagent: content (μg/cm$^2$) of reagent in reagent holding layer area (cm$^2$): area (cm$^2$) of reagent holding layer The components A, B, C, and D and the buffer in the measuring method of the present disclosure are identical to those in the test piece of the present disclosure. The ratio (D/C) of the component D to the component C in the test piece, and the contents of the components A, B, C, and D are identical to those of the test piece of the present disclosure.

One embodiment of the measuring method of the present disclosure is described below.

[Component D: Polyoxyethylene (23) Lauryl Ether]

The measuring method of the present disclosure, in one aspect, uses polyoxyethylene (23) lauryl ether as the component D.

Therefore, the present disclosure, in another aspect, relates to a method for measuring an amount of albumin based on measured values of optical properties of BCP under the presence of a protein denaturation agent and an SH reagent. The measuring method of the present disclosure comprises spotting a predetermined amount of a sample on a reagent holding layer of a test piece, the reagent holding layer containing a protein denaturation agent (component A), an SH reagent (component B), BCP (component C), and polyoxyethylene (23) lauryl ether (component D), and forming a mixture solution in which the sample and the components A, B, C, and D are mixed. In the mixture solution, a ratio (D/C, weight ratio) of the component D to the component C is 1.3 to 13, a concentration of the component C is 0.4 μg/μL to 5 μg/μL, and a concentration of the component D is 20 μg/μL or less.

In the present aspect, from the viewpoint of enabling the measurement at a high accuracy while suppressing influences of hemoglobin in a sample, the concentration of the component C in mixture solution is preferably 0.4 μg/μL to 5 μg/μL, and from the viewpoint of enabling the measurement at a higher accuracy while further suppressing influences of hemoglobin in a sample, the concentration is preferably 0.5 μg/μL to 4.3 μg/μL. From the viewpoint of enabling the obtainment of a higher sensitivity with respect to albumin and enabling the measurement of albumin at a higher accuracy even with respect to a sample with hemolysis, the concentration is more preferably 1.6 μg/μL to 3.8 μg/μL.

In the present aspect, from the viewpoint of enabling the measurement at a high accuracy while suppressing influences of hemoglobin in a sample, the concentration of the component D in mixture solution is preferably 20 μg/μL or less, and from the viewpoint of enabling the measurement at a higher accuracy while further suppressing influences of hemoglobin in a sample, the concentration is preferably 1.3 μg/μL to 20 μg/μL. From the viewpoint of enabling the obtainment of a higher sensitivity with respect to albumin and enabling the measurement of albumin at a higher accuracy even with respect to a sample with hemolysis, the concentration is more preferably 3.8 μg/μL to 8.8 μg/μL.

In the present aspect, the ratio (D/C weight ratio) of the component D to the component C in the mixture solution and a preferable range of the ratio are identical to those of the above-described test piece containing polyoxyethylene (23) lauryl ether as the component D. In the present aspect, the respective concentrations of the components A and B in the mixture solution are as described above.

[Component D: Polyoxyethylene Distyrenated Phenyl Ether]

The measuring method of the present disclosure, in one aspect, uses polyoxyethylene distyrenated phenyl ether as the component D. In the present aspect, the concentration of the component C in the mixture solution is preferably 0.5 μg/μL to 5.4 μg/μL, from the viewpoint of enabling the measurement at a higher accuracy while further suppressing influences of hemoglobin in a sample. From the viewpoint of enabling the obtainment of a higher sensitivity with respect to albumin and enabling the measurement of albumin at a higher accuracy even with respect to a sample with hemolysis, the concentration is more preferably 2.2 μg/μL to 5.4 μg/μL.

In the present aspect, the concentration of the component D in the mixture solution is preferably 23.0 μg/μL or less, from the viewpoint of enabling the measurement at a higher accuracy while further suppressing influences of hemoglobin in a sample. From the viewpoint of enabling the obtainment of a higher sensitivity with respect to albumin and enabling the measurement of albumin at a higher accuracy even with respect to a sample with hemolysis, the concentration is more preferably 12.5 μg/μL or less, and further preferably 3.8 μg/μL to 12.5 μg/μL.

In the present aspect, the ratio (D/C, weight ratio) of the component D to the component C in the mixture solution and a preferable range of the ratio are identical to those of the above-described test piece containing polyoxyethylene distyrenated phenyl ether as the component D. In the present aspect, the respective concentrations of the components A and B in the mixture solution are as described above.
[Component D: Polyoxyethylene (13) Oleyl Ether]

The measuring method of the present disclosure, in one aspect, uses polyoxyethylene (13) oleyl ether as the component D. In the present aspect, the concentration of the component C in the mixture solution is preferably 0.5 μg/μL to 5.4 μg/μL, from the viewpoint of enabling the measurement at a higher accuracy while further suppressing influences of hemoglobin in a sample. From the viewpoint of enabling the obtainment of a higher sensitivity with respect to albumin and enabling the measurement of albumin at a higher accuracy even with respect to a sample with hemolysis, the concentration is more preferably 2.2 μg/μL to 5.4 μg/μL.

In the present aspect, the concentration of the component D in the mixture solution is preferably 12.5 μg/μL or less, from the viewpoint of enabling the measurement at a higher accuracy while further suppressing influences of hemoglobin in a sample. From the viewpoint of enabling the obtainment of a higher sensitivity with respect to albumin and enabling the measurement of albumin at a higher accuracy even with respect to a sample with hemolysis, the concentration is more preferably 3.8 μg/μL to 12.5 μg/μL.

In the present aspect, the ratio (D/C weight ratio) of the component D to the component C in the mixture solution and a preferable range of the ratio are identical to those of the above-described test piece containing polyoxyethylene (13) oleyl ether as the component D. In the present aspect, the respective concentrations of the components A and B in the mixture solution are as described above.
[Component D: Polyoxyethylene Polyoxypropylene Alkyl Ether]

The measuring method of the present disclosure, in one aspect, uses polyoxyethylene polyoxypropylene alkyl ether as the component D. In the present aspect, the concentration of the component C in the mixture solution is preferably 2.2 μg/μL to 5.4 μg/μL, from the viewpoint of enabling the measurement at a higher accuracy while further suppressing influences of hemoglobin in a sample.

In the present aspect, from the viewpoint of enabling the measurement at a higher accuracy while further suppressing influences of hemoglobin in a sample, the concentration of the component D in the mixture solution is preferably 12.5 μg/μL or less, and more preferably 3.8 μg/μL to 12.5 μg/μL.

In the present aspect, the ratio (D/C weight ratio) of the component D to the component C in the mixture solution and a preferable range of the ratio are identical to those of the above-described test piece containing polyoxyethylene polyoxypropylene alkyl ether as the component D. In the present aspect, the respective concentrations of the components A and B in the mixture solution are as described above.
[Component D: Polyoxyethylene (20) Sorbitan Monolaurate]

The measuring method of the present disclosure, in one aspect, uses polyoxyethylene (20) sorbitan monolaurate as the component D. In the present aspect, the concentration of the component C in the mixture solution is preferably 2.2 μg/μL to 4.3 μg/μL, from the viewpoint of enabling the measurement at a higher accuracy while further suppressing influences of hemoglobin in a sample.

In the present aspect, from the viewpoint of enabling the measurement at a higher accuracy while further suppressing influences of hemoglobin in a sample, the concentration of the component D in the mixture solution is preferably 10.0 μg/μL or less, and more preferably 3.8 μg/μL to 10.0 μg/μL.

In the present aspect, the ratio (D/C weight ratio) of the component D to the component C in the mixture solution and a preferable range of the ratio are identical to those of the above-described test piece containing polyoxyethylene (20) sorbitan monolaurate as the component D. In the present aspect, the respective concentrations of the components A and B in the mixture solution are as described above.
[Component D: Polyoxyethylene (12) Lauryl Ether]

The measuring method of the present disclosure, in one aspect, uses polyoxyethylene (12) lauryl ether as the component D. In the present aspect, the concentration of the component C in the mixture solution is preferably 2.2 μg/μL to 4.3 μg/μL, from the viewpoint of enabling the measurement at a higher accuracy while further suppressing influences of hemoglobin in a sample. From the viewpoint of enabling the obtainment of a higher sensitivity with respect to albumin and enabling the measurement of albumin at a higher accuracy even with respect to a sample with hemolysis, the content is more preferably 2.2 μg/μL to 3.1 μg/μL.

In the present aspect, from the viewpoint of enabling the measurement at a higher accuracy while further suppressing influences of hemoglobin in a sample, the concentration of the component D in the mixture solution is preferably 5.0 μg/μL or less. From the viewpoint of enabling the obtainment of a higher sensitivity with respect to albumin and enabling the measurement of albumin at a higher accuracy even with respect to a sample with hemolysis, the content is more preferably 1.3 μg/μL to 3.8 μg/μL.

In the present aspect, the ratio (D/C weight ratio) of the component D to the component C in the mixture solution and a preferable range of the ratio are identical to those of the above-described test piece containing polyoxyethylene (12) lauryl ether as the component D. In the present aspect, the respective concentrations of the components A and B in the mixture solution are as described above.
[Component D: Polyoxyethylene (20) Sorbitan Monooleate]

The measuring method of the present disclosure, in one aspect, uses polyoxyethylene (20) sorbitan monooleate as the component D. In the present aspect, from the viewpoint of enabling the measurement at a higher accuracy while further suppressing influences of hemoglobin in a sample, the concentration of the component C in mixture solution is preferably 0.5 μg/μL to 5.4 μg/μL, and from the viewpoint of enabling the obtainment of a higher sensitivity with respect to albumin and enabling the measurement of albumin at a higher accuracy even with respect to a sample with hemolysis, the concentration is more preferably 2.2 μg/μL to 5.4 μg/μL.

When the measurement is performed using a test piece of the present disclosure containing polyoxyethylene (20) sorbitan monooleate as the component D, it is possible to sufficiently dissolve the component C in a sample and measure albumin at a high accuracy, even in a case where the content of the component D relative to the amount of the spotted sample in the reagent holding layer exceeds 25 μg/μL, for example, it is 30 μg/μL.

In the present aspect, from the viewpoint of enabling the measurement at a higher accuracy while further suppressing influences of hemoglobin in a sample, the concentration of the component D in mixture solution is preferably 30 μg/μL or less, 25 μg/μL or less, or 23.0 μg/μL or less, and from the viewpoint of enabling the obtainment of a higher sensitivity with respect to albumin and enabling the measurement of albumin at a higher accuracy even with respect to a sample with hemolysis, the concentration is more preferably 12.5 μg/μL or less, and further preferably 2.5 μg/μL to 12.5 μg/μL.

The present disclosure, in another aspect, relates to a method for measuring an amount of albumin based on measured values of optical properties of BCP under the presence of a protein denaturation agent and an SH reagent. The measuring method of the present disclosure comprises spotting a predetermined amount of a sample on a reagent holding layer of a test piece, the reagent holding layer containing a protein denaturation agent (component A), an SH reagent (component B), BCP (component C), and polyoxyethylene (20) sorbitan monooleate (component D), and forming a mixture solution in which the sample and the components A, B, C, and D are mixed. In the mixture solution, a ratio (D/C, weight ratio) of the component D to the component C is 1.2 to 13.9, a concentration of the component C is 0.5 µg/µL to 5.4 µg/µL, and a concentration of the component D is 30 µg/µL or less.

In the present aspect, the ratio (D/C weight ratio) of the component D to the component C in the mixture solution and a preferable range of the ratio are identical to those of the above-described test piece containing polyoxyethylene (20) sorbitan monooleate as the component D. In the present aspect, the respective concentrations of the components A and B in the mixture solution are as described above.

[Method for Producing Test Piece for Albumin Measurement]

The present disclosure, in another aspect, relates to a method for producing a test piece for albumin measurement of the present disclosure. The method of the present disclosure for producing a test piece, in some of embodiments, comprises: preparing an impregnating solution by mixing a protein denaturation agent (component A), an SH reagent (component B), BCP (component C), and a nonionic surfactant (component D); impregnating a reagent holding member with the impregnating solution; drying the impregnating solution that the reagent holding member is impregnated with; and attaching, to a support, the reagent holding member impregnated with the impregnating solution. The preparation of the impregnating solution is performed in such a manner that a ratio (D/C, weight ratio) of the component D to the component C is 0.3 to 13, a concentration of the component C is 0.4 µg/µL to 5.4 µg/µL with respect to an amount of a spotted sample when the test piece is used, and a concentration of the component D with respect to the amount of the spotted sample when the test piece is used is 25 µg/µL or less.

The respective concentrations of the components C and D with respect to the amount of the spotted sample when the test piece is used in the producing method of the present disclosure, and preferable ranges of the same, are identical to the concentrations thereof in the mixture solution in the measuring method of the present disclosure. The ratio (D/C, weight ratio) of the component D to the component C in the producing method of the present disclosure, and preferable ranges of the same, are identical to those of the test piece of the present disclosure.

The present disclosure, in another aspect, relates to a method for producing a test piece for albumin measurement of the present disclosure. The method of the present disclosure for producing a test piece, in some of embodiments, comprises: preparing an impregnating solution by mixing a protein denaturation agent (component A), an SH reagent (component B), BCP (component C), and polyoxyethylene (23) lauryl ether (component D); impregnating a reagent holding member with the impregnating solution; drying the impregnating solution that the reagent holding member is impregnated with; and attaching, to a support, the reagent holding member impregnated with the impregnating solution. The preparing of the impregnating solution is performed in such a manner that a ratio (D/C, weight ratio) of the component D to the component C is 1.3 to 13, a concentration of the component C with respect to an amount of a spotted sample when the test piece is used is 0.4 µg/µL to 5 µg/µL, and a concentration of the component D with respect to the amount of the spotted sample when the test piece is used is 20 µg/µL or less.

The method of the present disclosure for producing a test piece, in some of embodiments, may be characterized in that the preparing of the impregnating solution includes adjusting an impregnated amount so that the concentration of the component A with respect to the amount of the spotted sample when the test piece is used is 0.1 µg/µL to 15 µg/µL. The method of the present disclosure for producing a test piece, in some of embodiments, may be characterized in that the preparing of the impregnating solution is performed so that the concentration of the component B with respect to the amount of the spotted sample when the test piece is used is 0.0004 µg/µL to 8 µg/µL.

The method of the present disclosure for producing a test piece, in some of embodiments, may be characterized in that the preparing of the impregnating solution further includes mixing the components A, B, C, and D with a buffer. The buffer is, in some of embodiments, preferably mixed with the components A, B, C, and D in such a manner that, when the test piece is used, the reagent holding layer after the sample is spotted (the mixture solution) has a pH of 4.5 to 6.0, and preferably 5.0 to 5.5.

Embodiment 1

Figure 1B:
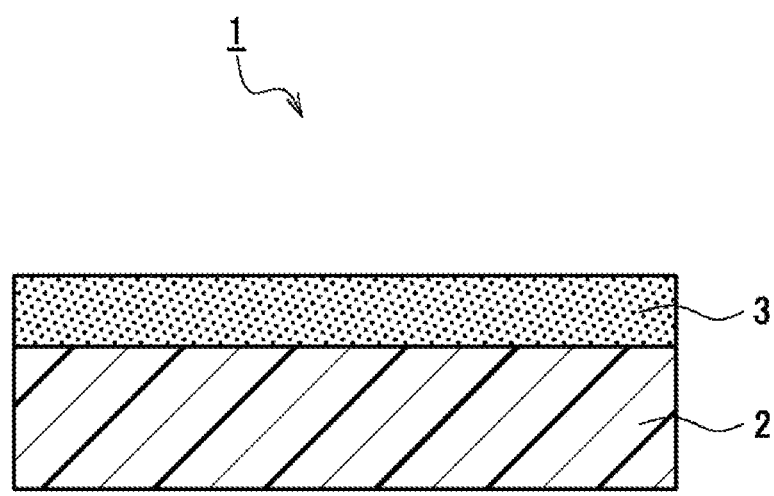

A test piece 1 for albumin measurement according to Embodiment 1 is formed with a support 2 in a thin and long rectangular shape, and a reagent holding layer 3 formed at one end thereof, as illustrated in FIG. 1A. As illustrated in FIG. 1B, the reagent holding layer 3 is arranged on the support 2 and bonded thereto with an adhesive (not shown) or the like interposed therebetween.

The test piece 1 for albumin measurement according to Embodiment 1 is produced as follows. In the Embodiment 1, an example in which polyoxyethylene (23) lauryl ether is used as the component D is described.

The support 2 is produced first. The support 2 is produced by cutting a PET sheet into a thin and long piece having a predetermined size. The width and length of the support 2 can be determined appropriately according to the amount of a sample used in the measurement. The width of the support 2 is about 5 mm to 1 cm in a case where the amount of a sample spotted is about 5 µL. The length of the support 2 is about 5 cm to 15 cm.

Next, the reagent holding layer 3 is produced. An impregnating solution that the reagent holding layer is to be impregnated with is prepared. BCP (component C), polyoxyethylene (23) lauryl ether (product name: Brij 35) (component D), 1 M succinic acid/NaOH buffer solution pH 5.5, SDS (component A), and DTNB (component B) are added sequentially in the stated order to distilled water, and are stirred to be dispersed, whereby the impregnating solution is prepared. Here, the preparation is carried out in such a manner that, in the impregnating solution, a ratio (D/C, weight ratio) of the component D to the component C is 1.3 to 13, a concentration of the component C with respect to the amount of a spotted sample when the test piece is used is 0.4 µg/µL to 5 µg/µL, and a concentration of the component D with respect to the amount of a spotted sample when the test piece is used is 20 µg/µL or less. The succinic acid/NaOH buffer solution is added to the impregnating solution so that a reaction solution after a sample is spotted (a mixture solution of a sample and the reagents) has a pH of 4.5 to 6.0, preferably 5.0 to 5.5.

The impregnating solution thus prepared is absorbed in a reagent holding member made of a material having a liquid penetration property such as a fabric material, whereby the reagents contained in the impregnating solution is dispersed in the reagent holding member. Then, it is dried so that moisture is removed, and is cut out into a predetermined size, whereby the reagent holding layer 3 is produced. The size of the reagent holding layer 3 can be determined appropriately according to the width of the support 2 and the amount of a sample used in the measurement. When the amount of a sample to be tested is about 5 $\mu$L, the size of the reagent holding layer 3 is about 5 mm to 10 mm×5 mm to 10 mm. The reagent holding layer 3 has a thickness of about 100 $\mu$m to 500 $\mu$m.

Next, the reagent holding layer 3 is arranged on the support 2. The reagent holding layer 3 can be bonded on the support 2 with an adhesive or an agglutinant.

The test piece 1 for albumin measurement can be produced in this way.

The measurement of albumin using the test piece 1 for albumin measurement according to Embodiment 1 is carried out as follows.

A predetermined uniform amount (for example, about 5 $\mu$L) of serum is dropped on the reagent holding layer 3 (5 mm×7 mm, thickness: 235 $\mu$m). A sample in a liquid form is diffused instantly throughout the reagent holding layer 3, and integrates all of the reagents, whereby a mixture solution in which the reagents are dissolved in the sample (reaction solution) is prepared in the reagent holding layer 3. In some embodiment, a concentration of the component C in the mixture solution is 0.4 $\mu$g/$\mu$L to 5 $\mu$g/$\mu$L, and a concentration of the component D in the mixture solution is 20 $\mu$g/$\mu$L or less.

BCP (component C) tends to develop color with respect to oxidized albumin, rather than reduced albumin. Therefore, in the mixture solution, SDS (component A) denatures albumin, and DTNB (component B) forms a disulfide bond to denatured albumin or reduced albumin in a sample, thereby changing the same into oxidized albumin. BCP binds to albumin (oxidized albumin) to form a BCP-albumin composite, whereby the hue of the mixture solution changes from yellow to green. The reagent holding layer 3 containing the mixture solution, therefore, exhibits a hue change from yellow to green according to the concentration of albumin contained in the sample.

Then, the reagent holding layer 3 is irradiated with light, and an intensity of light reflected by the reagent holding layer or an intensity of light passing through the reagent holding layer is measured. The measurement can be carried out 120 seconds to 300 seconds after the sample is spotted, or preferably 180 seconds after the same. The wavelength may be any wavelength as long as the hue of the BCP-albumin composite can be measured, and the wavelength is 570 nm to 660 nm, and preferably 600 nm to 630 nm or in the vicinity of 610 nm. The measurement may be carried out at a temperature of 15° C. to 37° C.

A degree of color formation (K/S value) may be calculated by irradiating the reagent holding layer 3 with light and receiving reflected light from the reagent holding layer 3. The K/S value can be calculated by the Kubelka-Munk formula shown below, with the reflectance of visible light being given as "R":

$$K/S=(1-R)^2/2R$$

The intensity of light can be measured with use of a commercially available optical analyzer. In some of embodiments, the optical analyzer is SPOTCHEM (registered trademark) (produced by ARKRAY Inc.).

As in the test piece for albumin measurement of Embodiment 1 the reagent holding layer 3 contains the component C (BCP) and the component D (polyoxyethylene (23) lauryl ether, Brij 35) at a predetermined ratio, influences of hemoglobin can be suppressed without additional correction, even in a case where, for example, hemoglobin having a property of absorbing light having a wavelength in the vicinity of 610 nm, which is the above-described measurement wavelength, is contained in serum. Therefore, albumin in serum can be measured at a high accuracy, and preferably quantified.

In the Embodiment 1, an example in which polyoxyethylene (23) lauryl ether is used as the component D is described, but the component D in the present disclosure is not limited to this. The manufacture and measurement can be performed in the same manner, even when another component D (nonionic surfactant) is used.

In the Embodiment 1, an example in which a fabric material is used as a reagent holding member is described, but the material of the reagent holding member is not limited to this. Various materials that can hold reagents can be used, and the material may be a fibrous material such as filter paper.

In the Embodiment 1, an example in which the reagent holding member impregnated with an impregnating solution, as the reagent holding layer 3 is arranged on the support 2 is described, but the method for forming the reagent holding layer 3 is not limited to this. The reagent holding layer 3 may be formed directly on the support 2, by dropping the impregnating solution directly onto the support 2 and drying the same, without impregnating a reagent holding member with a reagent solution. In this case (in the case where the reagent holding layer 3 does not include a reagent holding member), a surface of the support 2 may be treated and made hydrophobic, or a cavity may be provided on the support 2, so that an impregnating solution or a sample dropped on the support 2 stays in a range of a predetermined area and is held thereon.

In the Embodiment 1, an example in which the amount of a sample dropped on the reagent holding layer 3 is about 5 $\mu$L is described, but the amount of a sample is not limited to this. The method of supplying a sample onto the reagent holding layer 3 is not limited to dropping a sample onto the reagent holding layer 3. A sample may be spotted on the reagent holding layer 3, or the reagent holding layer 3 may be immersed in a sample in a container so that the reagent holding layer 3 is impregnated with the sample.

In the Embodiment 1, an example in which the hue of BCP is measured using the reflectance of light projected to the reagent holding layer 3 is described, but the method for measuring the hue of BCP is not limited to this. The measurement may be performed using transmitted light.

The present disclosure may relate to one or a plurality of non-limiting embodiments described below:

[1] A test piece for measuring albumin contained in a sample, the test piece comprising:
a support; and
a reagent holding layer provided on the support and on which a sample is spotted,
wherein the reagent holding layer contains a protein denaturation agent (component A), an SH reagent (component B), bromcresol purple (component C), and a nonionic surfactant (component D),
wherein in the reagent holding layer,
a weight ratio (D/C) of the component D to the component C is 0.3 to 13,
a content of the component C relative to the amount of the spotted sample is 0.4 µg/µL to 5.4 µg/µL, and
a content of the component D relative to the amount of the spotted sample is 25 µg/µL or less.

[2] The test piece according to [1],
wherein the weight ratio (D/C) of the component D to the component C is 1.3 to 13,
the content of the component C relative to the amount of the spotted sample is 0.4 µg/µL to 5 µg/µL, and
the content of the component D relative to the amount of the spotted sample is 20 µg/µL or less.

[3] The test piece according to [1] or [2],
wherein the nonionic surfactant is a nonionic surfactant having a polyoxyethylene group.

[4] The test piece according to any one of [1] to [3],
wherein the nonionic surfactant has an HLB value of 13.4 to 16.9.

[5] The test piece according to any one of [1] to [4],
wherein the nonionic surfactant is at least one selected from the group consisting of polyoxyethylene (23) lauryl ether, polyoxyethylene distyrenated phenyl ether, polyoxyethylene (13) oleyl ether, polyoxyethylene polyoxypropylene alkyl ether, polyoxyethylene (20) sorbitan monolaurate, polyoxyethylene (12) lauryl ether, and polyoxyethylene (20) sorbitan monooleate.

[6] A test piece for measuring albumin contained in a sample, the test piece comprising:
a support; and
a reagent holding layer provided on the support and on which a sample is spotted,
wherein the reagent holding layer contains a protein denaturation agent (component A), an SH reagent (component B), bromcresol purple (component C), and polyoxyethylene (23) lauryl ether (component D),
wherein in the reagent holding layer,
a weight ratio (D/C) of the component D to the component C is 1.3 to 13,
a content of the component C relative to the amount of the spotted sample is 0.4 µg/µL to 5 µg/µL, and
a content of the component D relative to the amount of the spotted sample is 20 µg/µL or less.

[7] The test piece according to [6],
wherein the weight ratio (D/C) of the component D to the component C is 1.5 to 9.3, and the content of the component C relative to the amount of the spotted sample is 0.5 µg/µL to 4.3 µg/µL.

[8] The test piece according to [6],
wherein the weight ratio (D/C) of the component D to the component C is 1.5 to 2.9, and the content of component C relative to the amount of the spotted sample is 1.6 µg/µL to 3.8 µg/µL.

[9] A test piece for measuring albumin contained in a sample, the test piece comprising:
a support; and
a reagent holding layer provided on the support and on which a sample is t spotted,
wherein the reagent holding layer contains a protein denaturation agent (component A), an SH reagent (component B), bromcresol purple (component C), and polyoxyethylene distyrenated phenyl ether (component D),
wherein in the reagent holding layer,
a weight ratio (D/C) of the component D to the component C is 1.2 to 10.6,
a content of the component C relative to the amount of the spotted sample is 0.5 µg/µL to 5.4 µg/µL, and
a content of the component D relative to the amount of the spotted sample is 25 µg/µL or less.

[10] A test piece for measuring albumin contained in a sample, the test piece comprising:
a support; and
a reagent holding layer provided on the support and on which a sample is spotted
wherein the reagent holding layer contains a protein denaturation agent (component A), an SH reagent (component B), bromcresol purple (component C), and polyoxyethylene (13) oleyl ether (component D),
wherein in the reagent holding layer,
a weight ratio (D/C) of the component D to the component C is 0.9 to 9.3,
a content of the component C relative to the amount of the spotted sample is 0.5 µg/µL to 5.4 µg/µL, and
a content of the component D relative to the amount of the spotted sample is 25 µg/µL or less.

[11] A test piece for measuring albumin contained in a sample, the test piece comprising:
a support; and
a reagent holding layer provided on the support and on which a sample is spotted,
wherein the reagent holding layer contains a protein denaturation agent (component A), an SH reagent (component B), bromcresol purple (component C), and polyoxyethylene polyoxypropylene alkyl ether (component D),
wherein in the reagent holding layer,
a weight ratio (D/C) of the component D to the component C is 1.2 to 2.3,
a content of the component C relative to the amount of the spotted sample is 2.2 µg/µL to 5.4 µg/µL, and
a content of the component D relative to the amount of the spotted sample is 25 µg/µL or less.

[12] A test piece for measuring albumin contained in a sample, the test piece comprising:
a support; and
a reagent holding layer provided on the support and on which a sample is spotted,
wherein the reagent holding layer contains a protein denaturation agent (component A), an SH reagent (component B), bromcresol purple (component C), and polyoxyethylene (20) sorbitan monolaurate (component D),
wherein in the reagent holding layer,
a weight ratio (D/C) of the component D to the component C is 1.7 to 2.3,
a content of the component C relative to the amount of the spotted sample is 2.2 µg/µL to 4.3 µg/µL, and
a content of the component D relative to the amount of the spotted sample is 25 µg/µL or less.

[13] A test piece for measuring albumin contained in a sample, the test piece comprising:
a support; and
a reagent holding layer provided on the support and on which a sample is spotted, wherein the reagent holding layer contains a protein denaturation agent (component A), an SH reagent (component B), bromcresol purple (component C), and polyoxyethylene (12) lauryl ether (component D),
wherein in the reagent holding layer,
a weight ratio (D/C) of the component D to the component C is 1.2 to 2.3,
a content of the component C relative to the amount of the spotted sample is 2.2 µg/µL to 4.3 µg/µL, and
a content of the component D relative to the amount of the spotted sample is 25 µg/µL or less.

[14] A test piece for measuring albumin contained in a sample, the test piece comprising:
a support; and
a reagent holding layer provided on the support and on which a sample is spotted,
wherein the reagent holding layer contains a protein denaturation agent (component A), an SH reagent (component B), bromcresol purple (component C), and polyoxyethylene (20) sorbitan monooleate (component D),
wherein in the reagent holding layer,
a weight ratio (D/C) of the component D to the component C of 1.2 to 13.9,
a content of the component C relative to the amount of the spotted sample is 0.5 µg/µL to 5.4 µg/µL, and
a content of the component D relative to the amount of the spotted sample is 30 µg/µL or less.

[15] The test piece according to any one of [1] to [14], wherein the protein denaturation agent is an anionic surfactant.

[16] The test piece according to any one of [1] to [15], to be used for measuring albumin contained in a biological specimen.

[17] The test piece according to [16],
wherein the biological specimen is serum or plasma.

[18] A method for measuring an amount of albumin in a sample based on measured values of optical properties of bromcresol purple under the presence of a protein denaturation agent and an SH reagent, the method comprising:
spotting a predetermined amount of the sample on a reagent holding layer of a test piece, the reagent holding layer containing a protein denaturation agent (component A), an SH reagent (component B), bromcresol purple (component C), and a nonionic surfactant (component D), and
forming a mixture solution in which the sample, the component A, the component B, the component C, and the component D are mixed,
wherein in the mixture solution,
a weight ratio (D/C) of the component D to the component C is 0.3 to 13,
a concentration of the component C is 0.4 µg/µL to 5.4 µg/µL, and
a concentration of the component D is 25 µg/µL or less.

[19] A method for measuring an amount of albumin in a sample based on measured values of optical properties of bromcresol purple under the presence of a protein denaturation agent and an SH reagent, the method comprising:
spotting a predetermined amount of the sample on a reagent holding layer of a test piece, the reagent holding layer containing a protein denaturation agent (component A), an SH reagent (component B), bromcresol purple (component C), and polyoxyethylene (23) lauryl ether (component D), and
forming a mixture solution in which the sample, the component A, the component B, the component C, and the component D are mixed,
wherein in the mixture solution,
a weight ratio (D/C) of the component D to the component C is 1.3 to 13,
a content of the component C relative to the amount of the spotted sample is 0.4 µg/µL to 5 µg/µL, and
a content of the component D relative to the amount of the spotted sample is 20 µg/µL or less.

[20] A method for measuring an amount of albumin in a sample based on measured values of optical properties of bromcresol purple under the presence of a protein denaturation agent and an SH reagent, the method comprising:
spotting a predetermined amount of the sample on a reagent holding layer of a test piece, the reagent holding layer containing a protein denaturation agent (component A), an SH reagent (component B), bromcresol purple (component C), and polyoxyethylene distyrenated phenyl ether (component D), and
forming a mixture solution in which the sample, the component A, the component B, the component C, and the component D are mixed,
wherein in the mixture solution,
a weight ratio (D/C) of the component D to the component C of 1.2 to 10.6,
a content of the component C relative to the amount of the spotted sample is 0.5 µg/µL to 5.4 µg/µL, and
a content of the component D relative to the amount of the spotted sample is 25 µg/µL or less.

[21] A method for measuring an amount of albumin in a sample based on measured values of optical properties of bromcresol purple under the presence of a protein denaturation agent and an SH reagent, the method comprising:
spotting a predetermined amount of the sample on a reagent holding layer of a test piece, the reagent holding layer containing a protein denaturation agent (component A), an SH reagent (component B), bromcresol purple (component C), and polyoxyethylene (13) oleyl ether (component D), and
forming a mixture solution in which the sample, the component A, the component B, the component C, and the component D are mixed,
wherein in the mixture solution,
a weight ratio (D/C) of the component D to the component C of 0.9 to 9.3,
a content of the component C relative to the amount of the spotted sample is 0.5 µg/µL to 5.4 µg/µL, and
a content of the component D relative to the amount of the spotted sample is 25 µg/µL or less.

[22] A method for measuring an amount of albumin in a sample based on measured values of optical properties of bromcresol purple under the presence of a protein denaturation agent and an SH reagent, the method comprising:
spotting a predetermined amount of the sample on a reagent holding layer of a test piece, the reagent holding layer containing a protein denaturation agent (component A), an SH reagent (component B), bromcresol purple (component C), and polyoxyethylene polyoxypropylene alkyl ether (component D), and forming a mixture solution in which the sample, the component A, the component B, the component C, and the component D are mixed,
wherein in the mixture solution,
a weight ratio (D/C) of the component D to the component C is 1.2 to 2.3,
a content of the component C relative to the amount of the spotted sample is 2.2 µg/µL to 5.4 µg/µL, and
a content of the component D relative to the amount of the spotted sample is 25 µg/µL or less.

[23] A method for measuring an amount of albumin in a sample based on measured values of optical properties of bromcresol purple under the presence of a protein denaturation agent and an SH reagent, the method comprising:
spotting a predetermined amount of the sample on a reagent holding layer of a test piece, the reagent holding layer containing a protein denaturation agent (component A), an SH reagent (component B), bromcresol purple (component C), and polyoxyethylene (20) sorbitan monolaurate (component D), and
forming a mixture solution in which the sample, the component A, the component B, the component C, and the component D are mixed,
wherein in the mixture solution,
a weight ratio (D/C) of the component D to the component C is 1.7 to 2.3,
a content of the component C relative to the amount of the spotted sample is 2.2 µg/µL to 4.3 µg/µL, and
a content of the component D relative to the amount of the spotted sample is 25 µg/µL or less.

[24] A method for measuring an amount of albumin in a sample based on measured values of optical properties of bromcresol purple under the presence of a protein denaturation agent and an SH reagent, the method comprising:
spotting a predetermined amount of the sample on a reagent holding layer of a test piece, the reagent holding layer containing a protein denaturation agent (component A), an SH reagent (component B), bromcresol purple (component C), and polyoxyethylene (12) lauryl ether (component D), and
forming a mixture solution in which the sample, the component A, the component B, the component C, and the component D are mixed,
wherein in the mixture solution,
a weight ratio (D/C) of the component D to the component C is 1.2 to 2.3,
a content of the component C relative to the amount of the spotted sample is 2.2 µg/µL to 4.3 µg/µL, and
a content of the component D relative to the amount of the spotted sample is 25 µg/µL or less.

[25] A method for measuring an amount of albumin in a sample based on measured values of optical properties of bromcresol purple under the presence of a protein denaturation agent and an SH reagent, the method comprising:
spotting a predetermined amount of the sample on a reagent holding layer of a test piece, the reagent holding layer containing a protein denaturation agent (component A), an SH reagent (component B), bromcresol purple (component C), and polyoxyethylene (20) sorbitan monooleate (component D), and
forming a mixture solution in which the sample, the component A, the component B, the component C, and the component D are mixed,
wherein in the mixture solution,
a weight ratio (D/C) of the component D to the component C is 1.2 to 13.9,
a content of the component C relative to the amount of the spotted sample is 0.5 µg/µL to 5.4 µg/µL, and
a content of the component D relative to the amount of the spotted sample is 30 µg/µL or less.

[26] The method according to any one of [18] to [25], the test piece comprises a support; and the reagent holding layer on which the sample is to be spotted is provided on the support.

[27] The method according to any one of [18] to [25], wherein the test piece is the test piece according to any one of [1] to [17].

[28] The method according to any one of [18] to [26], wherein the protein denaturation agent is an anionic surfactant.

[29] The method according to any one of [18] to [27], wherein the sample is a biological specimen.

[29] The method according to [28],
wherein the biological specimen is serum or plasma.

Hereinafter, although the following description describes the present disclosure in more detail by way of examples and comparative examples, these are illustrative, and the present disclosure is not limited to these examples.

EXAMPLES

[Production 1 of Test Piece for Albumin Measurement]

BCP, Brij 35 (polyoxyethylene (23) lauryl ether, nonionic surfactant, HLB: 16.9), 1 M succinic acid/NaOH buffer solution (pH 5.5), SDS (protein denaturation agent), and DTNB (5,5'-dithiobis(2-nitrobenzoic acid), SH reagent) were added sequentially to distilled water, whereby the impregnating solution was prepared. A fabric knitted with a composite yarn of polyester and nylon (thickness: 235 µm) was entirely uniformly impregnated with the impregnating solution thus prepared. The succinic acid/NaOH buffer solution was added to the impregnating solution so that a reaction solution after a sample was spotted onto the reagent holding layer (a mixture solution of a sample and the reagents) had a pH of 5.5.

The fabric thus impregnated was dried at 50° C. for ten minutes, and was cut into a size of 5 mm×7 mm, whereby a reagent holding layer was produced. The reagent holding layer 3 thus produced was attached onto a white PET plate 2 of 70 mm in length×5 mm in width with an adhesive, whereby a test piece 1 for albumin measurement shown in FIG. 1 was obtained. Contents of the reagents contained in the obtained test piece (reagent holding layer) are shown in Table 1 below. The concentration of mixture solution (when measured) in Table 1 refers to concentration of a reaction solution after a sample was spotted onto the reagent holding layer, i.e. a concentration of a mixture solution of the sample and the reagents.

TABLE 1

| Reagent | Content per unit area of reagent holding layer | Concentration of mixture solution (when measured) |
| --- | --- | --- |
| BCP (component C) | 30.9 µg/cm² | 2.2 µg/µL |
| Brij 35 (component D) | 71.4 µg/cm² | 5 µg/µL |
| 1 M succinic acid/NaOH buffer solution pH 5.5 | 5 µmol/cm² | 0.35 µmol/µL |
| SDS (component A) | 71.4 µg/cm² | 5 µg/µL |
| DTNB (component B) | 22.7 µg/cm² | 1.6 µg/µL |

[Preparation of Specimens]

The following reagents were appropriately mixed to prepare specimens 1 to 6 shown in Table 2 below.
Frozen pooled serum (3.9 g/dL albumin, 0 g/dL hemoglobin; Consera (registered trademark), produced by Nissui Pharmaceutical Co., Ltd.)
physiological saline solution
human serum albumin (Sigma-Aldrich Co. LLC)
hemolytic hemoglobin (interference check: A+, Sysmex Corporation)

TABLE 2

| Sample | | Concentration of albumin [g/dL] | Concentration of hemoglobin [g/dL] |
|---|---|---|---|
| Specimen 1 | Physiological saline solution | 0 | 0 |
| Specimen 2 | Pooled serum | 3.9 | 0 |
| Specimen 3 | Pooled serum + albumin | 6.5 | 0 |
| Specimen 4 | Pooled serum + Physiological saline solution | 1 | 0 |
| Specimen 5 | Pooled serum + Physiological saline solution | 3.5 | 0 |
| Specimen 6 | Pooled serum + hemoglobin | 3.5 | 0.5 |

[Preparation of Calibration Curve]

K/S values were calculated from specimens 1 to 3 and a calibration curve was prepared in the following procedure.

Specimens, 5 μL each, were spotted on the reagent holding layers of the test pieces for albumin measurement. Each reagent holding layer was irradiated with light having a wavelength of 610 nm for 180 seconds after the spotting, an intensity of reflected light of the irradiated light having a wavelength of 610 nm was measured, and a reflectance R as a ratio of the measured intensity of reflected light to the intensity of irradiation light was calculated. Degrees of coloration (K/S value) of the reagent holding layers were calculated from the reflectances R by the Kubelka-Munk formula, and the calibration curve was determined. The obtained K/S values and the calibration curve are shown in Table 3 below.

The measurement of the reflectance (reflected light) was performed with use of SPOTCHEM (registered trademark) D-Concept (produced by ARKRAY Inc.) under the following conditions.

[Measurement Parameters]
Main wavelength: 610 nm
Sub-wavelength: 810 nm
Measurement end time: 180 seconds
Measuring method: End point assay
Sample amount: 5 μL Kubelka-Munk formula: $K/S=(1-R)^2/2R$

TABLE 3

| Specimen | Concentration of albumin [g/dL] | K/S value |
|---|---|---|
| Specimen 1 | 0 | 0.1190 |
| Specimen 2 | 3.9 | 1.575 |
| Specimen 3 | 6.5 | 2.402 |

Calibration curve: $y=0.2118x^2+2.3002x-0.2768$ y: concentration of albumin [g/dL]
x: K/S value

[Method for Measurement of Serum Albumin Having Unknown Concentration]

Using a specimen 5 (concentration of albumin: 3.5 g/dL), measurement was carried out by the above-described method, and a K/S value was calculated. Using the calculated K/S value and the above-described calibration curve, the concentration of albumin was determined. As a result, the concentration of albumin was calculated to be 3.4 g/dL, with an error within ±3%, which means that the measurement was carried out at a high accuracy.

[Production 2 of Test Piece for Albumin Measurement]

Test pieces for albumin measurement (albumin test pieces) (Examples 1 to 21 and Reference Examples 1 to 3) containing Brij 35 and BCP at the contents and ratios shown in Table 4 below were prepared. The test pieces were prepared by the same procedure as that of Production 1 of test piece for albumin measurement described above. The content (test piece) in Table 4 refers to content of reagents per unit area of a reagent holding layer.

[Evaluation of Albumin Test Piece]

The test pieces for albumin measurement having different contents of BCP (component C) and Brij 35 (component D) (content relative to spotted sample amount) shown in Table 4 below were evaluated based on the following three items.
Item 1) concentration linearity
Item 2) measurement sensitivity
Item 3) precision (accuracy) when a sample with hemolysis is measured The contents of the buffer (1 M succinic acid/NaOH buffer solution (pH 5.5)), SDS (component A), and DTNB (component B) in Table 4 below were identical to those in Production 1 of test piece for albumin measurement described above (Table 1).

Item 1) Concentration Linearity

Measurement of albumin were carried out by the above-described method, using the test pieces shown in Table 4 and the specimens 1 to 3, and K/S values were calculated. A calibration curve was prepared using the calculated K/S values and the concentrations of albumin of the specimens 1 to 3. The concentrations of albumin of the specimens 2 and 3 were calculated from the obtained calibration curve and the K/S values of the specimens 2 and 3. Evaluation of concentration linearity of each test piece was carried out using the obtained concentrations of albumin based on evaluation criteria shown below.

The above-described measurement and evaluation were carried out as to each test piece shown in Table 4 below. The results are shown in Table 4 below. The K/S values shown in Table 4 are K/S values calculated from the measured values of the specimen 3.

<Evaluation Criteria>
Good:
the concentration of albumin calculated from the measured value of the specimen 2 was within 3.9 g/dL±15%, and
the concentration of albumin calculated from the measured value of the specimen 3 was within 6.5 g/dL±15%
Poor:
Other than the above Item 2) Measurement Sensitivity The above-described measurement using the specimen 1 (concentration of albumin: 0 g/dL) was carried out three times, K/S values were calculated, and a mean value thereof and a standard deviation (SD) were determined. Further, the above-described measurement using the specimen 4 (concentration of albumin: 1 g/dL) was carried out three times, K/S values were calculated, and a mean value thereof and a standard deviation (SD) were determined. Evaluation was carried out using the obtained mean value of the K/S values and the standard deviation (SD) based on evaluation criteria shown below, and measurement sensitivity of each test piece was evaluated.

The above-described measurement and evaluation were carried out as to each test piece shown in Table 4 below. The results are shown in Table 4 below.

<Evaluation Criteria>

Good:

The range of "(K/S value 1)+3×standard deviation (SD1)" and the range of "(K/S value 4)-3×standard deviation (SD4)" do not overlap at all.

Poor:

The range of "(K/S value 1)+3×standard deviation (SD1)" and the range of "(K/S value 4)-3×standard deviation (SD4)" partly overlap.

the calibration curve prepared using the specimens 1 to 3. A rate of divergence (%) was calculated by the formula shown below, using the calculated concentrations of albumin of the specimens 5 and 6, and evaluation was carried out using the obtained rate of divergence (%) based on evaluation criteria shown below, so that regarding each test piece, precision in the measurement of a sample with hemolysis was evaluated. The specimen 6 had a concentration of hemoglobin of 0.5 g/dL, which is a concentration recommended by CLSI (Clinical and Laboratory Standards Institute) EP07-A2.

Rate of divergence (%)={(albumin concentration 6)−(albumin concentration 5)}/(albumin concentration 5)×100

Albumin concentration 5: concentration of albumin calculated from the K/S value of the specimen 5

Albumin concentration 6: concentration of albumin calculated from the K/S value of the specimen 6

<Evaluation Criteria>

Good: the rate of divergence is 15% or less.

Poor: the rate of divergence exceeds 15%.

TABLE 4

| Test piece | | BCP (Comp. C) Content (test piece) [µg/cm$^2$] | Brij35 (Comp. D) [µg/cm$^2$] | BCP (Comp. C) Concentration in mixture solution (when measured) [µg/µL] | Brij35 (Comp. D) [µg/µL] | D/C (Weight ratio) | 1) Concentration linearity | 2) Measurement sensitivity | 3) Precision (Accuracy) | Evaluation | K/S value |
|---|---|---|---|---|---|---|---|---|---|---|---|
| Example | 1 | 46.3 | 71.4 | 3.2 | 5.0 | 1.5 | Good | Good | Good | ◎ | 2.936 |
| | 2 | 30.9 | 53.6 | 2.2 | 3.8 | 1.7 | Good | Good | Good | ◎ | 2.544 |
| | 3 | 38.6 | 89.3 | 2.7 | 6.3 | 2.3 | Good | Good | Good | ◎ | 2.553 |
| | 4 | 54.0 | 125.0 | 3.8 | 8.8 | 2.3 | Good | Good | Good | ◎ | 2.735 |
| | 5 | 30.9 | 71.4 | 2.2 | 5.0 | 2.3 | Good | Good | Good | ◎ | 2.402 |
| | 6 | 7.7 | 17.9 | 0.5 | 1.3 | 2.3 | Good | Good | Good | ◎ | 1.160 |
| | 7 | 15.4 | 35.7 | 1.1 | 2.5 | 2.3 | Good | Good | Good | ◎ | 1.789 |
| | 8 | 23.2 | 53.6 | 1.6 | 3.8 | 2.3 | Good | Good | Good | ◎ | 2.232 |
| | 9 | 46.3 | 107.1 | 3.2 | 7.5 | 2.3 | Good | Good | Good | ◎ | 2.486 |
| | 10 | 61.7 | 142.9 | 4.3 | 10.0 | 2.3 | Good | Good | Good | ◎ | 0.980 |
| | 11 | 30.9 | 89.3 | 2.2 | 6.3 | 2.9 | Good | Good | Good | ◎ | 2.233 |
| | 12 | 30.9 | 107.1 | 2.2 | 7.5 | 3.5 | Good | Good | Good | ◎ | 2.155 |
| | 13 | 15.4 | 71.4 | 1.1 | 5.0 | 4.6 | Good | Good | Good | ◎ | 1.634 |
| | 14 | 30.9 | 142.9 | 2.2 | 10.0 | 4.6 | Good | Good | Good | ◎ | 1.812 |
| | 15 | 7.7 | 71.4 | 0.5 | 5.0 | 9.3 | Good | Good | Good | ◎ | 0.978 |
| | 16 | 30.9 | 285.7 | 2.2 | 20.0 | 9.3 | Good | Good | Good | ◎ | 2.168 |
| | 17 | 15.4 | 142.9 | 1.1 | 10.0 | 9.3 | Good | Good | Good | ◎ | 1.656 |
| | 18 | 30.9 | 35.7 | 2.2 | 2.5 | 1.2 | Good | Good | Poor | ○ | 0.138 |
| | 19 | 61.7 | 71.4 | 4.3 | 5.0 | 1.2 | Good | Good | Poor | ○ | 0.416 |
| | 20 | 77.2 | 178.6 | 5.4 | 12.5 | 2.3 | Good | Good | Poor | ○ | 0.344 |
| | 21 | 61.7 | 328.6 | 4.3 | 23.0 | 5.3 | Good | Good | Poor | ○ | 0.473 |
| Ref. Ex. | 1 | 3.9 | 8.9 | 0.3 | 0.6 | 2.3 | Good | Good | Poor | ○ | 0.610 |
| | 2 | 30.9 | 428.6 | 2.2 | 30.0 | 13.9 | Good | Good | Poor | ○ | 0.177 |
| | 3 | 3.9 | 71.4 | 0.3 | 5.0 | 18.5 | Good | Good | Poor | ○ | 0.628 |

K/S value 1: mean value of K/S values of the specimen 1

K/S value 4: mean value of K/S values of the specimen 4

SD1: standard deviation (SD) of the specimen 1

SD4: standard deviation (SD) of the specimen 4

Item 3) Precision (Accuracy) when a Sample with Hemolysis is Measured

Measurement of albumin were carried out using the specimens 1 to 3 and K/S values were calculated by the method described above in the section of [Preparation of calibration curve], and a calibration curve was prepared.

Figure 2:
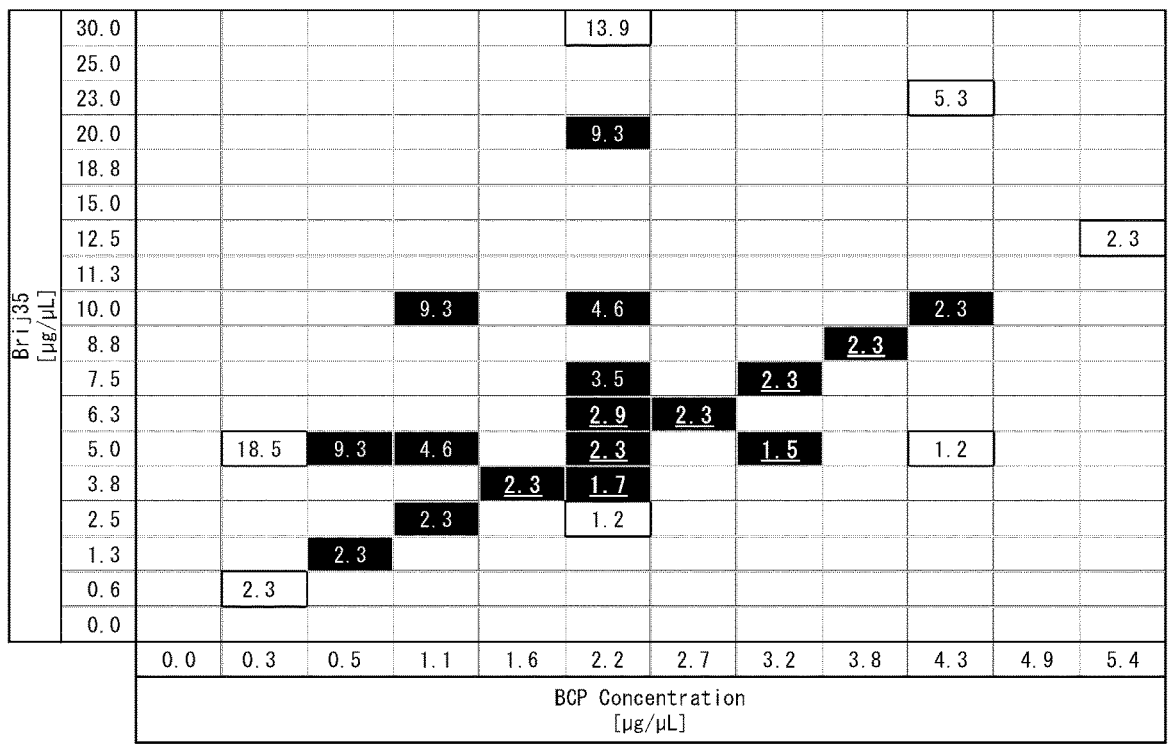
FIG. 2 shows each ratio (D/C) between the content of BCP (component C) and the content of polyoxyethylene (23) lauryl ether (Brij 35) (component D) relative to the amount of a spotted sample in a test piece for albumin measurement based on Example, and evaluation thereof.
Figure 3:
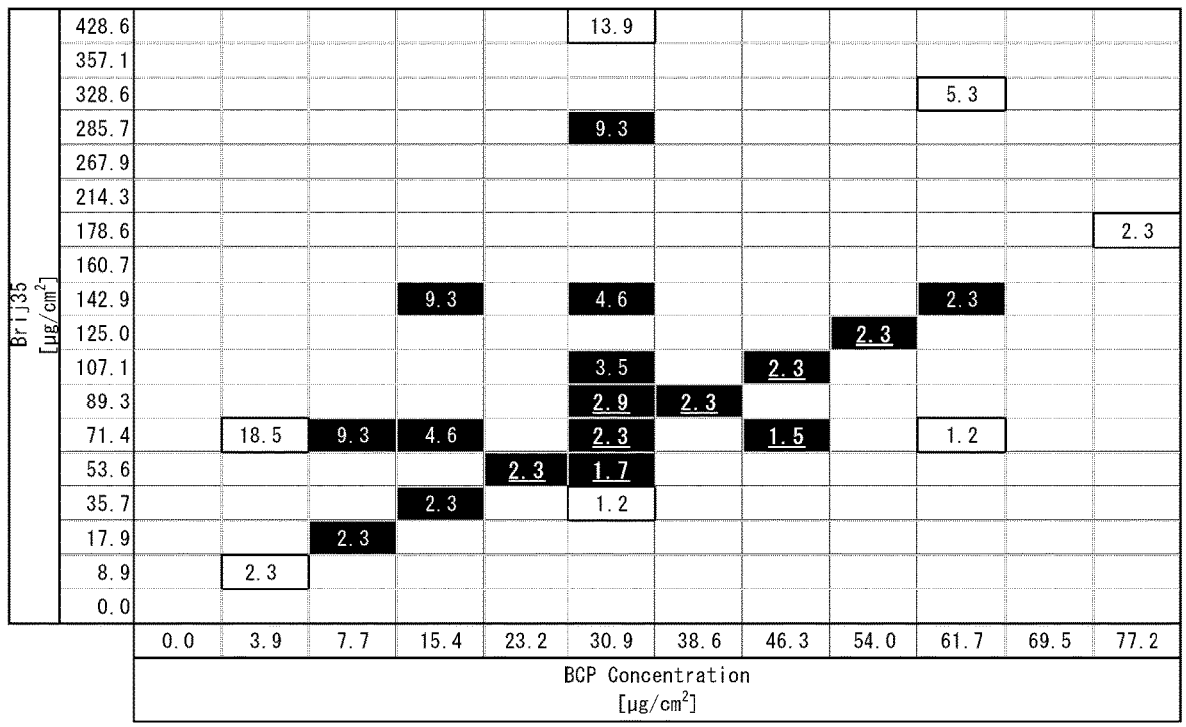
FIG. 3 shows each ratio (D/C) between the content of BCP (component C) and the content of polyoxyethylene (23) lauryl ether (Brij 35) (component D) per unit area of a sample spot surface (surface on which a sample is spotted) of a reagent holding layer in a test piece for albumin measurement based on Example, and evaluation thereof.

Next, using the specimens 5 and 6 (in both cases, the concentration of albumin was 3.5 g/dL), measurement of albumin concentrations was carried out by the same method as above, and K/S values were calculated. The concentrations of albumin of the specimens 5 and 6 were calculated from the obtained K/S values of the specimens 5 and 6 and The evaluation results of the albumin test pieces shown in Table 4 are plotted, with the content of BCP (µg/µL) relative to the amount of the spotted sample being taken as the horizontal axis, and the content of Brij 35 (µg/µL) relative to the amount of the spotted sample being taken as the vertical axis, and the diagram obtained is shown in FIG. 2. The same evaluation results are plotted with the content of BCP (µg/cm$^2$) per unit area of the reagent holding layer being taken as the horizontal axis, and the content of Brij 35 (µg/cm$^2$) per unit area of the reagent holding layer being taken as the vertical axis, and the diagram obtained is shown in FIG. 3. In FIGS. 2 and 3, cells corresponding to the test pieces evaluated as "C)" in Table 4 above are indicated with black color, and cells corresponding to the test pieces evaluated as "0" are indicated with white color. The numerical value shown in each cell indicates the ratio of the content of Brij 35 to the content of BCP (D/C, weight ratio). The evaluation results shown in Table 4 are as follows.

⊚: All of evaluation results regarding the evaluation items 1) to 3) are good.

○: Evaluation results regarding the evaluation items 1) and 2) are good.

x: Only an evaluation result regarding the evaluation item 1) is good, or all of evaluation results regarding the evaluation items 1) to 3) are poor.

From the above-described evaluation and FIGS. 2 and 3, it was confirmed that any dry test piece satisfying the following conditions enables the measurement of the concentration of albumin at a high accuracy, even if serum containing hemoglobin is measured.

D/C (Brij 35/BCP, weight ratio): 1.5 to 9.3

Concentration of BCP: 0.5 to 4.3 µg/µL (content: 7.7 to 61.7 µg/cm$^2$)

Concentration of Brij 35: 20 µg/µL or less (content: 285.7 µg/cm$^2$ or less)

In FIGS. 2 and 3, the test pieces of Examples satisfying the conditions, with the values of D/C being underlined, had K/S values of 2.2 or more when measuring the specimen 3 having a concentration of albumin of 6.5 g/dL (concentration of hemoglobin: 0 g/dL). These test pieces (Examples 1 to 5, 8, 9, and 11) exhibited high K/S values with respect to albumin, among the test pieces of Examples 1 to 21. That the test pieces having the underlined D/C values exhibited higher K/S values in spite of measuring specimens having the same concentration of albumin means that the test pieces had high sensitivity with respect to albumin, and it can be said that a change in the K/S value leads to only a small change in the measured value of albumin (concentration of albumin calculated from the K/S value). Therefore, the test pieces having the underlined D/C values, satisfying the following conditions, enable the measurement of albumin at a higher accuracy even with respect to serum containing a large amount of hemoglobin.

D/C (Brij 35/BCP, weight ratio): 1.5 to 2.9

Concentration of BCP: 1.6 to 3.8 µg/µL

Concentration of Brij 35: 3.8 to 8.8 µg/µL

[Test Regarding Correlation with Liquid Reagent of Improved BCP Method]

Serum sampled from 48 patients with consent was measured with use of a liquid reagent of the improved BCP method that is an existing product, and test pieces of Example 5. The measurement with the liquid reagent was carried out according to the document attached to the product. The test pieces of Example 5 were measured by the above-described method, and K/S values were obtained.

[Liquid Reagent]

Albumin kit for blood test, L-type Wako ALB-BCP (produced by FUJIFILM Wako Pure Chemical Corporation)

(Measurement principle: improved BCP method)

[Test Piece]

Test Pieces of Example 5

Figure 4:
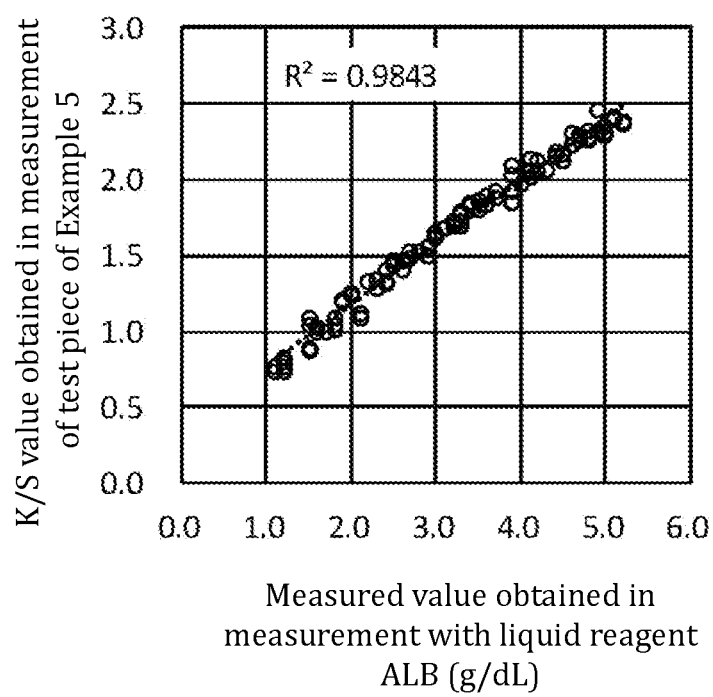
FIG. 4 is a graph showing an exemplary test result regarding the correlation between test pieces of Example 5 and a liquid reagent of the improved BCP method.

FIG. 4 shows correlation between measured values of the liquid reagent of the improved BCP method and K/S values of the test pieces of Example 5. The K/S values of the test pieces of Example 5 exhibited excellent correlation with respect to the measurement values of the liquid reagent of the improved BCP method. This proves that the test pieces of the present disclosure had excellent performance.

[Production 3 of Albumin Test Piece]

Dry test pieces for albumin measurement were prepared by the same procedure as that for Production 1 of test piece for albumin measurement described above, except that polyoxyethylene distyrenated phenyl ether (produced by Kao Corporation, Emulgen A90, HLB: 14.5) was used in place of Brij 35, and the contents and ratios of Emulgen A90 and BCP were set as shown in Table 5 below. The test pieces thus produced were evaluated regarding the above-described items 1) to 3). The results are shown in Table 5 below. The K/S values shown in Table 5 are K/S values calculated from the measured values of the specimen 3, and the evaluation results shown in Table 5 are as follows.

⊚: All of evaluation results regarding the evaluation items 1) to 3) are good.

○: Evaluation results regarding the evaluation items 1) and 2) are good.

x: Only an evaluation result regarding the evaluation item 1) is good, or all of evaluation results regarding the evaluation items 1) to 3) are poor.

TABLE 5

| Test piece | | Content (test piece) BCP [µg/cm$^2$] | Emulgen A90 [µg/cm$^2$] | Mixture solution (when measured) Conc. of BCP [µg/µL] | Conc. of Emulgen A90 [µg/µL] | Conc. of Emulgen A90/ Conc. of BCP | 1) Concentration linearity | 2) Measurement sensitivity | 3) Precision (accuracy) | Evaluation | k/s value |
|---|---|---|---|---|---|---|---|---|---|---|---|
| Example | 1-1 | 7.7 | 71.4 | 0.5 | 5.0 | 9.3 | Good | Good | Good | ⊚ | 0.861 |
| | 1-2 | 30.9 | 71.4 | 2.2 | 5.0 | 2.3 | Good | Good | Good | ⊚ | 2.338 |
| | 1-3 | 61.7 | 142.9 | 4.3 | 10.0 | 2.3 | Good | Good | Good | ⊚ | 3.008 |
| | 1-4 | 61.7 | 71.4 | 4.3 | 5.0 | 1.2 | Good | Good | Good | ⊚ | 3.182 |
| | 1-5 | 77.2 | 178.6 | 5.4 | 12.5 | 2.3 | Good | Good | Good | ⊚ | 2.615 |
| | 1-6 | 30.9 | 328.6 | 2.2 | 23.0 | 10.6 | Good | Good | Good | ⊚ | 1.221 |
| | 1-7 | 30.9 | 53.6 | 2.2 | 3.8 | 1.7 | Good | Good | Good | ⊚ | 2.382 |
| | 1-8 | 15.4 | 142.9 | 1.1 | 10.0 | 9.3 | Good | Good | Good | ⊚ | 0.774 |
| | 1-9 | 46.3 | 71.4 | 3.2 | 5.0 | 1.5 | Good | Good | Good | ⊚ | 2.711 |
| | 1-10 | 30.9 | 142.9 | 2.2 | 10.0 | 4.6 | Good | Good | Good | ⊚ | 1.085 |
| | 1-12 | 77.2 | 71.4 | 5.4 | 5.0 | 0.9 | Good | Good | Poor | ○ | 0.344 |
| | 1-13 | 3.9 | 8.9 | 0.3 | 0.6 | 2.3 | Good | Good | Poor | ○ | 0.480 |
| | 1-14 | 30.9 | 428.6 | 2.2 | 30.0 | 13.9 | Good | Good | Poor | ○ | 0.934 |
| | 1-15 | 30.9 | 8.9 | 2.2 | 0.6 | 0.3 | Good | Good | Poor | ○ | 0.190 |
| Ref. Ex. | 1-1 | 0.2 | 71.4 | 0.01 | 5.0 | 462.8 | Good | Poor | Poor | X | 0.010 |
| | 1-2 | 0.2 | 0.4 | 0.01 | 0.03 | 2.3 | Poor | Poor | Poor | X | 0.009 |

Figure 5:
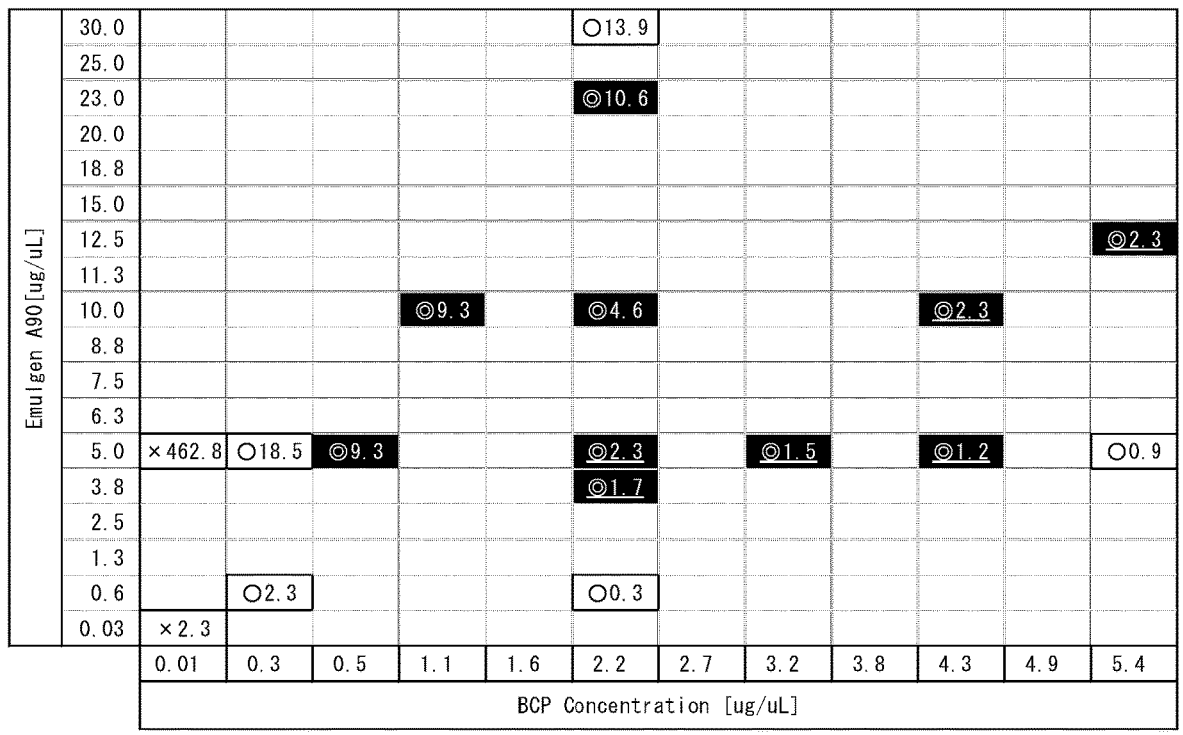
FIG. 5 shows each ratio (D/C) between the content of BCP (component C) and the content of polyoxyethylene distyrenated phenyl ether (Emulgen A90) (component D) relative to the amount of a spotted sample in a test piece for albumin measurement based on Example, and evaluation thereof.
Figure 6:
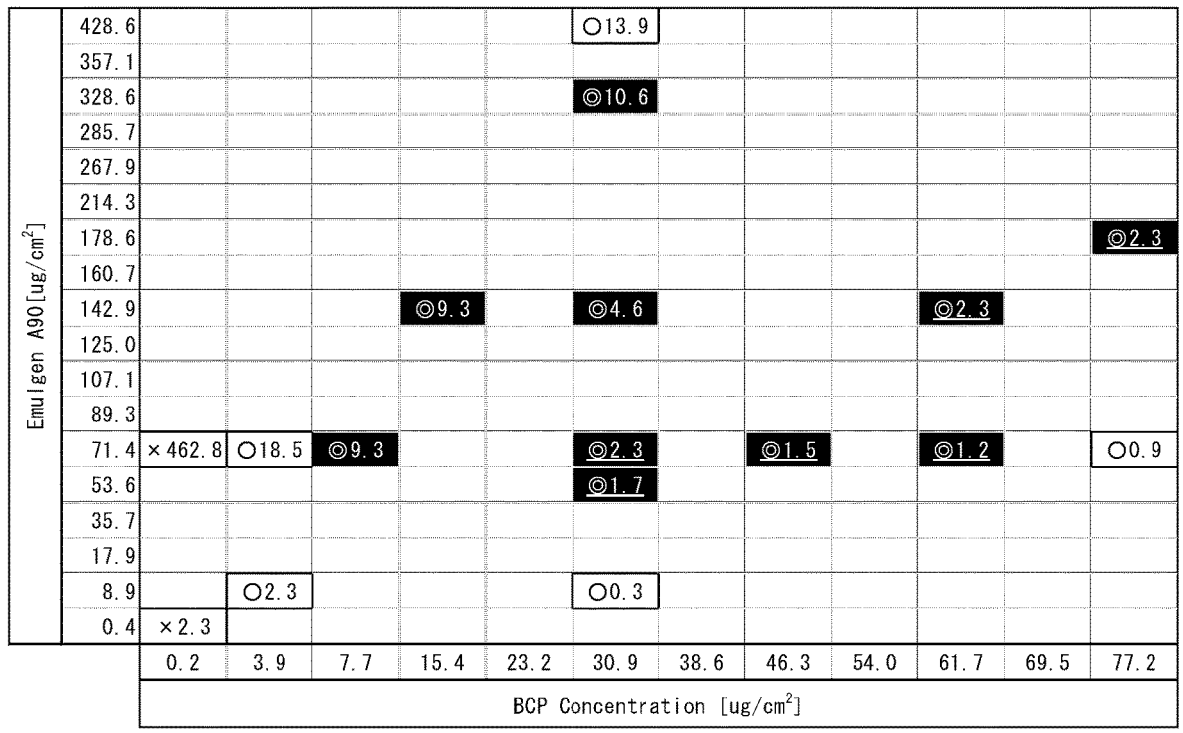
FIG. 6 shows each ratio (D/C) between the content of BCP (component C) and the content of polyoxyethylene distyrenated phenyl ether (Emulgen A90) (component D) per unit area of a sample spot surface (surface on which a sample is spotted) of a reagent holding layer in a test piece for albumin measurement based on Example, and evaluation thereof.

The evaluation results of the albumin test pieces shown in Table 5 are plotted, with the content of BCP (μg/μL) relative to the amount of the spotted sample being taken as the horizontal axis, and the content of Emulgen A90 (μg/μL) relative to the amount of the spotted sample being taken as the vertical axis, and the diagram obtained is shown in FIG. 5. The same evaluation results are plotted with the content of BCP (μg/cm$^2$) per unit area of the reagent holding layer being taken as the horizontal axis, and the content of Emulgen A90 (μg/cm$^2$) per unit area of the reagent holding layer being taken as the vertical axis, and the diagram obtained is shown in FIG. 6. The numerical value shown in each cell indicates the ratio of the content of Emulgen A90 to the content of BCP (D/C, weight ratio). In FIGS. 5 and 6, the test pieces of Examples satisfying the conditions, with the values of D/C being underlined, had K/S values of 2.2 or more when measuring the specimen 3.

As shown in Table 5 and FIGS. 5 and 6, all of the test pieces of Examples (Examples 1-1 to 1-15) as the dry test pieces containing Emulgen A90 as the component D had good evaluation regarding both of the evaluation items 1) and 2), which confirms that these test pieces enable the measurement of albumin at a high sensitivity. Besides, the test pieces exhibited high linearity, which proves that they enable the measurement of albumin at a high accuracy.

As shown in Table 5, regarding the dry test pieces containing Emulgen A90 as the component D, it was confirmed that any dry test piece satisfying the following conditions (Examples 1-1 to 1-10) enables the measurement of the concentration of albumin at a high accuracy, even if serum containing hemoglobin is measured.

D/C (Emulgen A90/BCP, weight ratio): 1.2 to 10.6
Concentration of BCP: 0.5 to 5.4 μg/μL (content: 7.7 to 77.2 μg/cm$^2$)
Concentration of Emulgen A90: 23 μg/μL or less (content: 328.6 μg/cm$^2$ or less)

The dry test pieces of Examples 1-2 to 1-5, 1-7, and 1-9 had K/S values of 2.2 or more when measuring the specimen 3 having a concentration of albumin of 6.5 g/dL (concentration of hemoglobin: 0 g/dL). Therefore, the test pieces satisfying the following conditions enables the measurement of albumin at a higher accuracy even with respect to serum containing a large amount of hemoglobin.

D/C (Emulgen A90/BCP, weight ratio): 1.2 to 2.3
Concentration of BCP: 2.2 to 5.4 μg/μL
Concentration of Emulgen A90: 12.5 μg/μL or less

[Production 4 of Albumin Test Piece]

Dry test pieces for albumin measurement were prepared by the same procedure as that for Production 1 of test piece for albumin measurement described above, except that polyoxyethylene (13) oleyl ether (produced by Kao Corporation, Emulgen 420, HLB: 13.6) was used in place of Brij 35, and the contents and ratios of Emulgen 420 and BCP were set as shown in Table 6 below. The test pieces thus produced were evaluated regarding the above-described items 1) to 3). The results are shown in Table 6 below. The K/S values shown in Table 6 are K/S values calculated from the measured values of the specimen 3, and the evaluation criteria used for the evaluation whose results are shown in Table 6 were the same as those for Production 3 of albumin test piece.

TABLE 6

| Test piece | Content (test piece) | | Mixture solution (when measured) | | Conc. of Emulgen 420/ Conc. of BCP | 1) Concentration linearity | 2) Measurement sensitivity | 3) Precision (accuracy) | Evaluation | k/s value |
|---|---|---|---|---|---|---|---|---|---|---|
| | BCP [μg/cm$^2$] | Emulgen 420 [μg/cm$^2$] | Conc. of BCP [μg/μL] | Conc. of Emulgen 420 [μg/μL] | | | | | | |
| Example 2-1 | 7.7 | 71.4 | 0.5 | 5.0 | 9.3 | Good | Good | Good | ⊚ | 0.763 |
| 2-2 | 30.9 | 71.4 | 2.2 | 5.0 | 2.3 | Good | Good | Good | ⊚ | 2.218 |
| 2-3 | 46.3 | 71.4 | 3.2 | 5.0 | 1.5 | Good | Good | Good | ⊚ | 2.899 |
| 2-4 | 7.7 | 17.9 | 0.5 | 1.3 | 2.3 | Good | Good | Good | ⊚ | 1.050 |
| 2-5 | 61.7 | 142.9 | 4.3 | 10.0 | 2.3 | Good | Good | Good | ⊚ | 3.099 |
| 2-6 | 30.9 | 142.9 | 2.2 | 10.0 | 4.6 | Good | Good | Good | ⊚ | 1.435 |
| 2-7 | 61.7 | 71.4 | 4.3 | 5.0 | 1.2 | Good | Good | Good | ⊚ | 3.475 |
| 2-8 | 77.2 | 71.4 | 5.4 | 5.0 | 0.9 | Good | Good | Good | ⊚ | 3.743 |
| 2-9 | 77.2 | 178.6 | 5.4 | 12.5 | 2.3 | Good | Good | Good | ⊚ | 3.220 |
| 2-10 | 30.9 | 53.6 | 2.2 | 3.8 | 1.7 | Good | Good | Good | ⊚ | 2.481 |
| 2-11 | 3.9 | 71.4 | 0.3 | 5.0 | 18.5 | Good | Good | Poor | ◯ | 0.526 |
| 2-12 | 3.9 | 8.9 | 0.3 | 0.6 | 2.3 | Good | Good | Poor | ◯ | 0.609 |
| 2-13 | 30.9 | 428.6 | 2.2 | 30.0 | 13.9 | Good | Good | Poor | ◯ | 0.771 |
| 2-14 | 30.9 | 8.9 | 2.2 | 0.6 | 0.3 | Good | Good | Poor | ◯ | 0.159 |
| Ref. Ex. 2-1 | 0.2 | 71.4 | 0.01 | 5.0 | 462.8 | Good | Poor | Poor | X | 0.012 |
| 2-2 | 0.2 | 0.4 | 0.01 | 0.03 | 2.3 | Good | Poor | Poor | X | 0.017 |

The evaluation results of the albumin test pieces shown in Table 6 are plotted, with the content of BCP (μg/μL) relative to the amount of the spotted sample being taken as the horizontal axis, and the content of Emulgen 420 (μg/μL) relative to the amount of the spotted sample being taken as the vertical axis, and the diagram obtained is shown in FIG. 7. The same evaluation results are plotted with the content of BCP (μg/cm$^2$) per unit area of the reagent holding layer being taken as the horizontal axis, and the content of Emulgen 420 (μg/cm$^2$) per unit area of the reagent holding layer being taken as the vertical axis, and the diagram obtained is shown in FIG. 8. The numerical value shown in each cell indicates the ratio of the content of Emulgen 420 to the content of BCP (D/C, weight ratio). In FIGS. 7 and 8, the test pieces of Examples satisfying the conditions, with the values of D/C being underlined, had K/S values of 2.2 or more when measuring the specimen 3.

As shown in Table 6 and FIGS. 7 and 8, all of the test pieces of Examples (Examples 2-1 to 2-14) as the dry test pieces containing Emulgen 420 as the component D had good evaluation regarding both of the evaluation items 1) and 2), which confirms that these test pieces enable the measurement of albumin at a high sensitivity. Besides, the test pieces exhibited high linearity, which proves that they enable the measurement of albumin at a high accuracy.

As shown in Table 6, regarding the dry test pieces containing Emulgen 420 as the component D, it was confirmed that any dry test piece satisfying the following conditions (Examples 2-1 to 2-10) enables the measurement of the concentration of albumin at a high accuracy, even if serum containing hemoglobin is measured.

D/C (Emulgen 420/BCP, weight ratio): 0.9 to 9.3
Concentration of BCP: 0.5 to 5.4 µg/µL (content: 7.7 to 77.2 µg/cm$^2$)
Concentration of Emulgen 420: 12.5 µg/µL or less (content: 178.6 µg/cm$^2$ or less)

The dry test pieces of Examples 2-2 to 2-5 and 2-7 to 2-10 had K/S values of 2.2 or more when measuring the specimen 3 having a concentration of albumin of 6.5 g/dL (concentration of hemoglobin: 0 g/dL). Therefore, with the test pieces satisfying the following conditions, albumin can be measured at a higher accuracy even with respect to serum containing a large amount of hemoglobin.

D/C (Emulgen 420/BCP, weight ratio): 0.9 to 2.3
Concentration of BCP: 2.2 to 5.4 µg/µL
Concentration of Emulgen 420: 3.8 to 12.5 µg/µL

[Production 5 of Albumin Test Piece]

Figure 9:
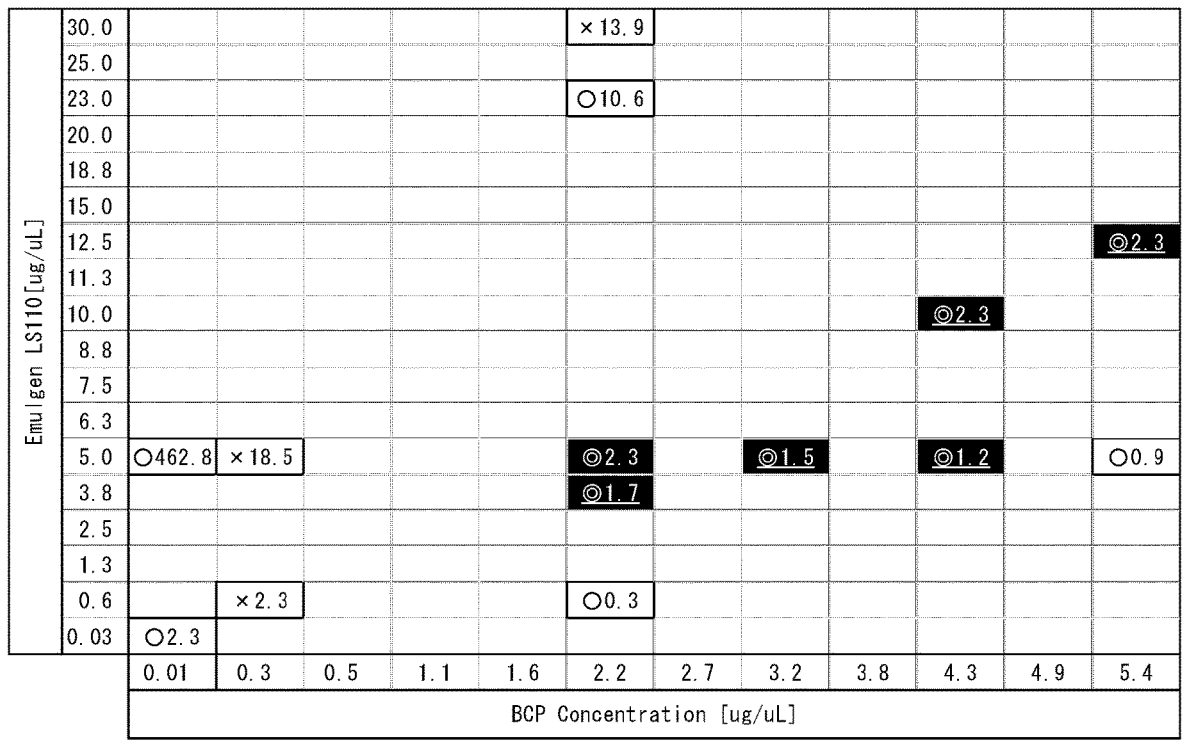
FIG. 9 shows each ratio (D/C) between the content of BCP (component C) and the content of polyoxyethylene polyoxypropylene alkyl ether (Emulgen LS110) (component D) relative to the amount of a spotted sample in a test piece for albumin measurement based on Example, and evaluation thereof.
Figure 10:
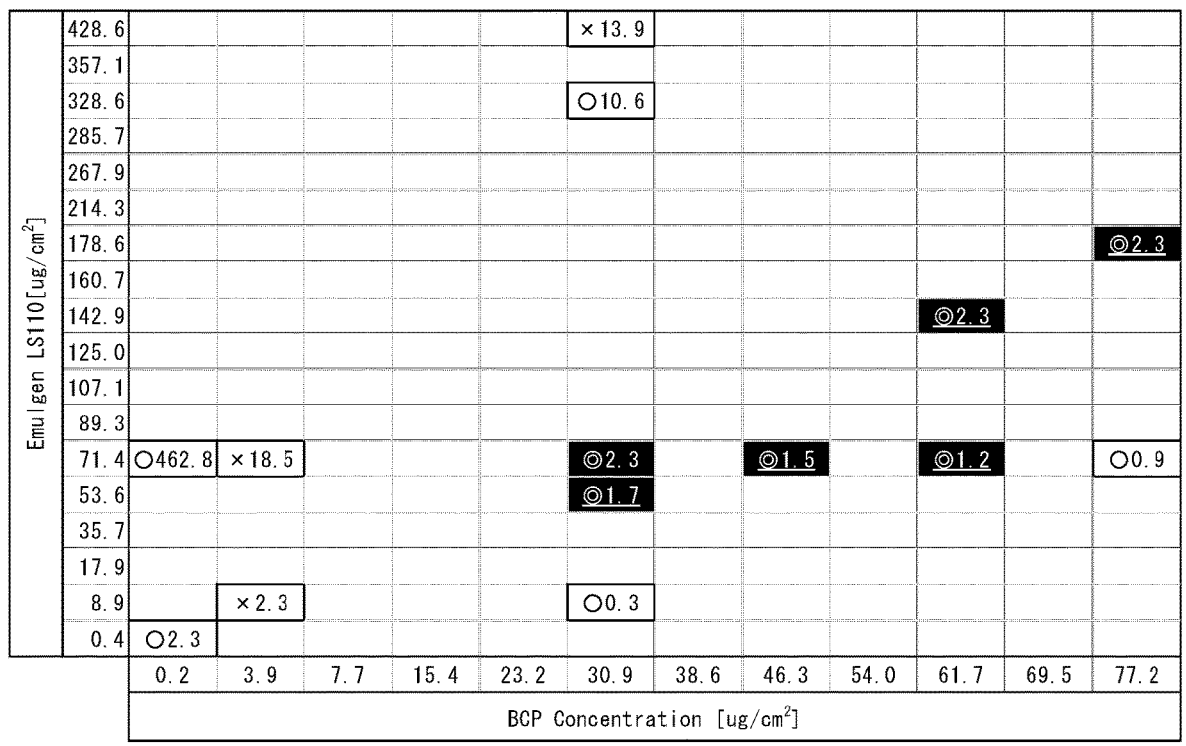
FIG. 10 shows each ratio (D/C) between the content of BCP (component C) and the content of polyoxyethylene polyoxypropylene alkyl ether (Emulgen LS110) (component D) per unit area of a sample spot surface (surface on which a sample is spotted) of a reagent holding layer in a test piece for albumin measurement based on Example, and evaluation thereof.

Dry test pieces for albumin measurement were prepared by the same procedure as that for Production 1 of test piece for albumin measurement described above, except that polyoxyethylene polyoxypropylene alkyl ether (produced by Kao Corporation, Emulgen LS110, HLB: 13.4) was used in place of Brij 35, and the contents and ratios of Emulgen LS110 and BCP were set as shown in Table 7 below. The test pieces thus produced were evaluated regarding the above-described items 1) to 3). The results are shown in Table 7 below. The K/S values shown in Table 7 are K/S values calculated from the measured values of the specimen 3, and the evaluation criteria used for the evaluation whose results are shown in Table 7 were the same as those for Production 3 of albumin test piece.

the vertical axis, and the diagram obtained is shown in FIG. 9. The same evaluation results are plotted with the content of BCP (µg/cm$^2$) per unit area of the reagent holding layer being taken as the horizontal axis, and the content of Emulgen LS110 (µg/cm$^2$) per unit area of the reagent holding layer being taken as the vertical axis, and the diagram obtained is shown in FIG. 10. The numerical value shown in each cell indicates the ratio of the content of Emulgen LS110 to the content of BCP (D/C, weight ratio). In FIGS. 9 and 10, the test pieces of Examples satisfying the conditions, with the values of D/C being underlined, had K/S values of 2.2 or more when measuring the specimen 3.

As shown in Table 7 and FIGS. 9 and 10, all of the test pieces of Examples (Examples 3-1 to 3-11) as the dry test pieces containing Emulgen LS110 as the component D had good evaluation regarding both of the evaluation items 1) and 2), which confirms that these test pieces enable the measurement of albumin at a high sensitivity. Besides, the test pieces exhibited high linearity, which proves that they enable the measurement of albumin at a high accuracy.

As shown in Table 7, regarding the dry test pieces containing Emulgen LS110 as the component D, it was confirmed that any dry test piece satisfying the following conditions (Examples 3-1 to 3-6) enables the measurement of the concentration of albumin at a high accuracy, even if serum containing hemoglobin is measured.

D/C (Emulgen LS110/BCP, weight ratio): 1.2 to 2.3
Concentration of BCP: 2.2 to 5.4 µg/µL (content: 30.9 to 77.2 µg/cm$^2$)
Concentration of Emulgen LS110: 12.5 µg/µL or less (content: 178.6 µg/cm$^2$ or less)

The test pieces satisfying the above-described conditions had K/S values of 2.2 or more, or close to 2.2, when measuring the specimen 3 having a concentration of albumin of 6.5 g/dL (concentration of hemoglobin: 0 g/dL). Therefore, the test pieces satisfying the above-described conditions enable the measurement of albumin at a higher accuracy even with respect to serum containing a large amount of hemoglobin.

TABLE 7

| Test piece | Content (test piece) BCP [µg/cm$^2$] | Content (test piece) Emulgen LS110 [µg/cm$^2$] | Mixture solution (when measured) Conc. of BCP [µg/µL] | Mixture solution (when measured) Conc. of Emulgen LS110 [µg/µL] | Conc. of Emulgen LS110/ Conc. of BCP | 1) Concentration linearity | 2) Measurement sensitivity | 3) Precision (accuracy) | Evaluation | k/s value |
|---|---|---|---|---|---|---|---|---|---|---|
| Example 3-1 | 46.3 | 71.4 | 3.2 | 5.0 | 1.5 | Good | Good | Good | ⊚ | 2.720 |
| 3-2 | 61.7 | 142.9 | 4.3 | 10.0 | 2.3 | Good | Good | Good | ⊚ | 2.787 |
| 3-3 | 30.9 | 71.4 | 2.2 | 5.0 | 2.3 | Good | Good | Good | ⊚ | 1.891 |
| 3-4 | 61.7 | 71.4 | 4.3 | 5.0 | 1.2 | Good | Good | Good | ⊚ | 3.495 |
| 3-5 | 77.2 | 178.6 | 5.4 | 12.5 | 2.3 | Good | Good | Good | ⊚ | 3.495 |
| 3-6 | 30.9 | 53.6 | 2.2 | 3.8 | 1.7 | Good | Good | Good | ⊚ | 2.380 |
| 3-7 | 0.2 | 71.4 | 0.01 | 5.0 | 462.0 | Good | Good | Poor | ○ | 0.010 |
| 3-8 | 77.2 | 71.4 | 5.4 | 5.0 | 0.9 | Good | Good | Poor | ○ | 3.707 |
| 3-9 | 0.2 | 0.4 | 0.01 | 0.03 | 2.3 | Good | Good | Poor | ○ | 0.017 |
| 3-10 | 30.9 | 328.6 | 2.2 | 23.0 | 10.6 | Good | Good | Poor | ○ | 0.696 |
| 3-11 | 30.9 | 8.9 | 2.2 | 0.6 | 0.3 | Good | Good | Poor | ○ | 0.171 |
| Ref. Ex. 3-1 | 30.9 | 428.6 | 2.2 | 30.0 | 13.9 | Good | Poor | Poor | X | 0.519 |
| 3-2 | 3.9 | 71.4 | 0.3 | 5.0 | 18.5 | Good | Poor | Poor | X | 0.467 |
| 3-3 | 3.9 | 8.9 | 0.3 | 0.6 | 2.3 | Good | Poor | Poor | X | 0.552 |

The evaluation results of the albumin test pieces shown in Table 7 are plotted, with the content of BCP (µg/µL) relative to the amount of the spotted sample being taken as the horizontal axis, and the content of Emulgen LS110 (µg/µL) relative to the amount of the spotted sample being taken as

[Production 6 of Albumin Test Piece]

Dry test pieces for albumin measurement were prepared by the same procedure as that for Production 1 of test piece for albumin measurement described above, except that polyoxyethylene (20) sorbitan monolaurate (Tween 20, HLB:

16.7) was used in place of Brij 35, and the contents and ratios of Tween 20 and BCP were set as shown in Table 8 below. The test pieces thus produced were evaluated regarding the above-described items 1) to 3). The results are shown in Table 8 below. The K/S values shown in Table 8 are K/S values calculated from the measured values of the specimen 3, and the evaluation criteria used for the evaluation whose results are shown in Table 8 were the same as those for Production 3 of albumin test piece.

TABLE 8

| Test piece | | Content (test piece) | | Mixture solution (when measured) | | Conc. of Tween 20/ Conc. of BCP | 1) Concentration linearity | 2) Measurement sensitivity | 3) Precision (accuracy) | Evaluation | k/s value |
|---|---|---|---|---|---|---|---|---|---|---|---|
| | | BCP [μg/cm²] | Tween 20 [μg/cm²] | Conc. of BCP [μg/μL] | Conc. of Tween 20 [μg/μL] | | | | | | |
| Example | 4-1 | 61.7 | 142.9 | 4.3 | 10.0 | 2.3 | Good | Good | Good | ◉ | 2.609 |
| | 4-2 | 30.9 | 53.6 | 2.2 | 3.8 | 1.7 | Good | Good | Good | ◉ | 2.421 |
| | 4-3 | 3.9 | 71.4 | 0.3 | 5.0 | 18.5 | Good | Good | Poor | ○ | 0.870 |
| | 4-4 | 61.7 | 71.4 | 4.3 | 5.0 | 1.2 | Good | Good | Poor | ○ | 3.449 |
| | 4-5 | 77.2 | 71.4 | 5.4 | 5.0 | 0.9 | Good | Good | Poor | ○ | 1.823 |
| | 4-6 | 77.2 | 178.6 | 5.4 | 12.5 | 2.3 | Good | Good | Poor | ○ | 2.078 |
| | 4-7 | 3.9 | 8.9 | 0.3 | 0.6 | 2.3 | Good | Good | Poor | ○ | 0.525 |
| | 4-8 | 30.9 | 428.6 | 2.2 | 30.0 | 13.9 | Good | Good | Poor | ○ | 0.928 |
| | 4-9 | 30.9 | 328.6 | 2.2 | 23.0 | 10.6 | Good | Good | Poor | ○ | 0.959 |
| | 4-10 | 30.9 | 35.7 | 2.2 | 2.5 | 1.2 | Good | Good | Poor | ○ | 0.405 |
| | 4-11 | 30.9 | 8.9 | 2.2 | 0.6 | 0.3 | Good | Good | Poor | ○ | 0.297 |
| Ref. Ex. | 4-1 | 0.2 | 71.4 | 0.01 | 5.0 | 462.8 | Good | Poor | Poor | X | 0.011 |
| | 4-2 | 0.2 | 0.4 | 0.01 | 0.03 | 2.3 | Good | Poor | Poor | X | 0.007 |

The evaluation results of the albumin test pieces shown in Table 8 are plotted, with the content of BCP (μg/μL) relative to the amount of the spotted sample being taken as the horizontal axis, and the content of Tween 20 (μg/μL) relative to the amount of the spotted sample being taken as the vertical axis, and the diagram obtained is shown in FIG. 11. The same evaluation results are plotted with the content of BCP (μg/cm²) per unit area of the reagent holding layer being taken as the horizontal axis, and the content of Tween 20 (μg/cm²) per unit area of the reagent holding layer being taken as the vertical axis, and the diagram obtained is shown in FIG. 12. The numerical value shown in each cell indicates the ratio of the content of Tween 20 to the content of BCP (D/C, weight ratio). In FIGS. 11 and 12, the test pieces of Examples satisfying the conditions, with the values of D/C being underlined, had K/S values of 2.2 or more when measuring the specimen 3.

As shown in Table 8 and FIGS. 11 and 12, all of the test pieces of Examples (Examples 4-1 to 4-11) as the dry test pieces containing Tween 20 as the component D had good evaluation regarding both of the evaluation items 1) and 2), which confirms that these test pieces enable the measurement of albumin at a high sensitivity. Besides, the test pieces exhibited high linearity, which proves that they enable the measurement of albumin at a high accuracy.

As shown in Table 8, regarding the dry test pieces containing Tween 20 as the component D, it was confirmed that any dry test piece satisfying the following conditions (Examples 4-1 and 4-2) enables the measurement of the concentration of albumin at a high accuracy, even if serum containing hemoglobin is measured.

D/C (Tween 20/BCP, weight ratio): 1.7 to 2.3

Concentration of BCP: 2.2 to 4.3 μg/μL (content: 30.9 to 61.7 μg/cm²)

Concentration of Tween 20: 10.0 μg/μL or less (content: 142.9 μg/cm² or less)

[Production 7 of Albumin Test Piece]

Dry test pieces for albumin measurement were prepared by the same procedure as that for Production 1 of test piece for albumin measurement described above, except that polyoxyethylene (12) lauryl ether (produced by Kao Corporation, Emulgen 120, HLB: 15.3) was used in place of Brij 35, and the contents and ratios of Emulgen 120 and BCP were set as shown in Table 9 below. The test pieces thus produced were evaluated regarding the above-described items 1) to 3). The results are shown in Table 9 below. The K/S values shown in Table 9 are K/S values calculated from the measured values of the specimen 3, and the evaluation criteria used for the evaluation whose results are shown in Table 9 were the same as those for Production 3 of albumin test piece.

TABLE 9

| Test piece | | Content (test piece) BCP [μg/cm²] | Emulgen 120 [μg/cm²] | Mixture solution (when measured) Conc. of BCP [μg/μL] | Conc. of Emulgen 120 [μg/μL] | Conc. of Emulgen 120/ Conc. of BCP | 1) Concentration linearity | 2) Measurement sensitivity | 3) Precision (accuracy) | Evaluation | k/s value |
|---|---|---|---|---|---|---|---|---|---|---|---|
| Example | 5-1 | 30.9 | 71.4 | 2.2 | 5.0 | 2.3 | Good | Good | Good | ⊚ | 1.555 |
| | 5-2 | 30.9 | 35.7 | 2.2 | 2.5 | 1.2 | Good | Good | Good | ⊚ | 2.459 |
| | 5-3 | 46.3 | 71.4 | 3.2 | 5.0 | 1.5 | Good | Good | Good | ⊚ | 1.845 |
| | 5-4 | 61.7 | 71.4 | 4.3 | 5.0 | 1.2 | Good | Good | Good | ⊚ | 2.035 |
| | 5-5 | 3.9 | 71.4 | 0.3 | 5.0 | 18.5 | Good | Good | Poor | ○ | 0.412 |
| | 5-6 | 77.2 | 71.4 | 5.4 | 5.0 | 0.9 | Good | Good | Poor | ○ | 3.383 |
| | 5-7 | 77.2 | 178.6 | 5.4 | 12.5 | 2.3 | Good | Good | Poor | ○ | 1.479 |
| | 5-8 | 3.9 | 8.9 | 0.3 | 0.8 | 2.3 | Good | Good | Poor | ○ | 0.499 |
| | 5-9 | 30.9 | 428.6 | 2.2 | 30.0 | 13.9 | Good | Good | Poor | ○ | 0.363 |
| | 5-10 | 30.9 | 328.6 | 2.2 | 23.0 | 10.6 | Good | Good | Poor | ○ | 0.537 |
| | 5-11 | 30.9 | 8.9 | 2.2 | 0.6 | 0.3 | Good | Good | Poor | ○ | 0.205 |
| Ref. Ex. | 5-1 | 0.2 | 71.4 | 0.01 | 5.0 | 462.8 | Good | Poor | Poor | X | 0.018 |
| | 5-2 | 0.2 | 0.4 | 0.01 | 0.03 | 2.3 | Good | Poor | Poor | X | 0.008 |

Figures 13, 14:
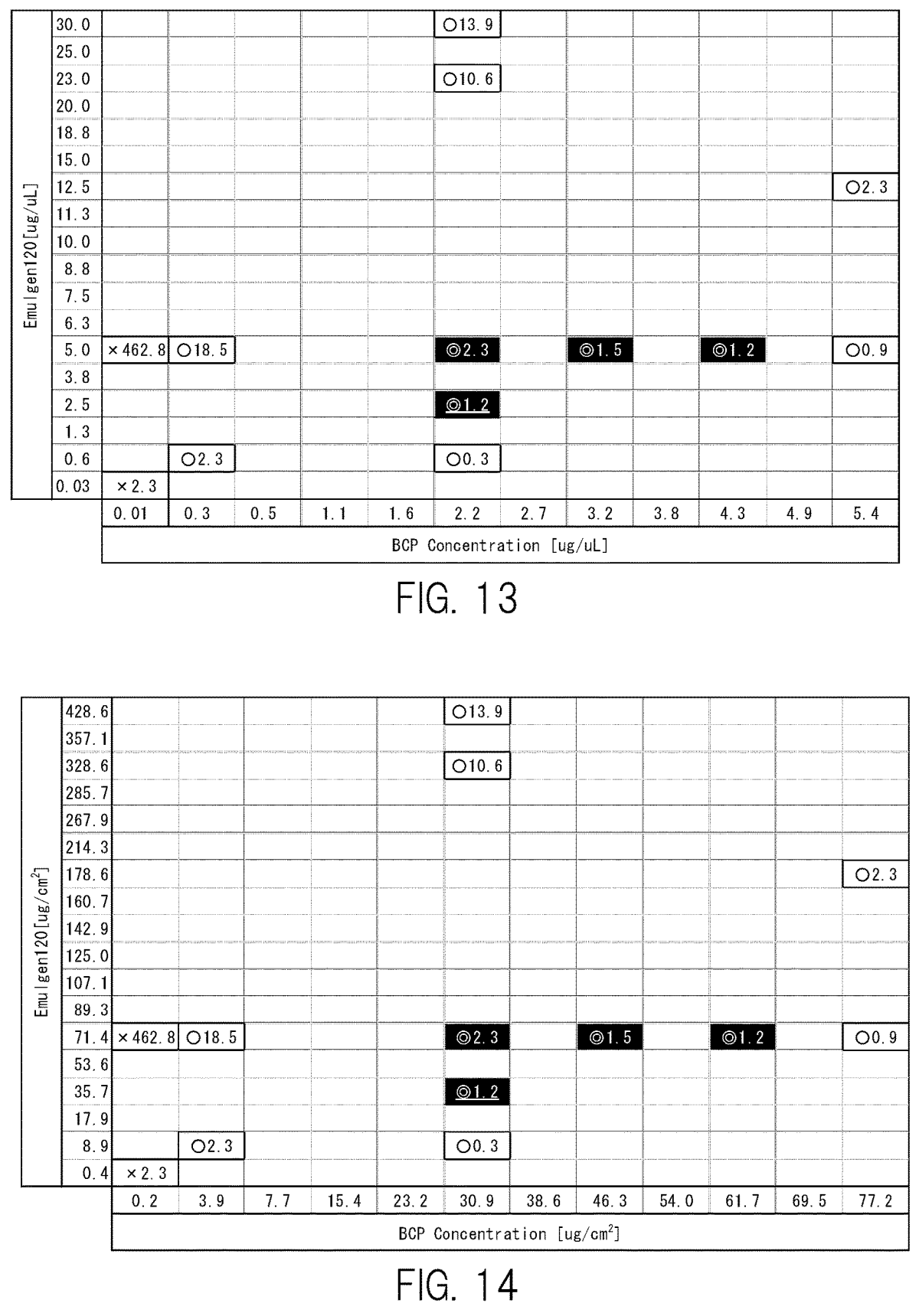

The evaluation results of the albumin test pieces shown in Table 9 are plotted, with the content of BCP (μg/μL) relative to the amount of the spotted sample being taken as the horizontal axis, and the content of Emulgen 120 (μg/μL) relative to the amount of the spotted sample being taken as the vertical axis, and the diagram obtained is shown in FIG. 13. The same evaluation results are plotted with the content of BCP (μg/cm²) per unit area of the reagent holding layer being taken as the horizontal axis, and the content of Emulgen 120 (μg/cm²) per unit area of the reagent holding layer being taken as the vertical axis, and the diagram obtained is shown in FIG. 14. The numerical value shown in each cell indicates the ratio of the content of Emulgen 120 to the content of BCP (D/C, weight ratio). In FIGS. 13 and 14, the test pieces of Examples satisfying the conditions, with the values of D/C being underlined, had K/S values of 2.2 or more when measuring the specimen 3.

As shown in Table 9 and FIGS. 13 and 14, all of the test pieces of Examples (Examples 5-1 to 5-11) as the dry test pieces containing Emulgen 120 as the component D had good evaluation regarding both of the evaluation items 1) and 2), which confirms that these test pieces enable the measurement of albumin at a high sensitivity. Besides, the test pieces exhibited high linearity, which proves that they enable the measurement of albumin at a high accuracy.

As shown in Table 9, regarding the dry test pieces containing Emulgen 120 as the component D, it was confirmed that any dry test piece satisfying the following conditions (Examples 5-1 to 5-4) enables the measurement of the concentration of albumin at a high accuracy, even if serum containing hemoglobin is measured.

D/C (Emulgen 120/BCP, weight ratio): 1.2 to 2.3
Concentration of BCP: 2.2 to 4.3 μg/μL (content: 7.7 to 77.2 μg/cm²)
Concentration of Emulgen 120: 5.0 μg/μL or less (content: 71.4 μg/cm² or less)

In Table 9 above, the dry test piece of Example 5-2 had a K/S value of 2.2 or more when measuring the specimen 3 having a concentration of albumin of 6.5 g/dL (concentration of hemoglobin: 0 g/dL). Therefore, with the test pieces satisfying the following conditions, albumin can be measured at a higher accuracy even with respect to serum containing a large amount of hemoglobin.

D/C (Emulgen 120/BCP, weight ratio): 1.2 to 1.4
Concentration of BCP: 2.2 to 3.1 μg/μL
Concentration of Emulgen 120: 1.3 to 3.8 μg/μL

[Production 8 of Albumin Test Piece]

Dry test pieces for albumin measurement were prepared by the same procedure as that for Production 1 of test piece for albumin measurement described above, except that polyoxyethylene (20) sorbitan monooleate (Tween 80, HLB: 15.0) was used in place of Brij 35, and the contents and ratios of Tween 80 and BCP were set as shown in Table 10 below. The test pieces thus produced were evaluated regarding the above-described items 1) to 3). The results are shown in Table 10 below. The K/S values shown in Table 10 are K/S values calculated from the measured values of the specimen 3, and the evaluation criteria used for the evaluation whose results are shown in Table 10 were the same as those for Production 3 of albumin test piece.

TABLE 10

| Test piece | | Content (test piece) BCP [μg/cm²] | Tween 80 [μg/cm²] | Mixture solution (when measured) Conc. of BCP [μg/μL] | Conc. of Tween 80 [μg/μL] | Tween 80/ Conc. of BCP | 1) Concentration linearity | 2) Measurement sensitivity | 3) Precision (accuracy) | Evaluation | k/s value |
|---|---|---|---|---|---|---|---|---|---|---|---|
| Example | 6-1 | 7.7 | 71.4 | 0.5 | 5.0 | 9.3 | Good | Good | Good | ⊚ | 0.944 |
| | 6-2 | 30.9 | 71.4 | 2.2 | 5.0 | 2.3 | Good | Good | Good | ⊚ | 2.268 |
| | 6-3 | 46.3 | 71.4 | 3.2 | 5.0 | 1.5 | Good | Good | Good | ⊚ | 2.501 |
| | 6-4 | 61.7 | 142.9 | 4.3 | 10.0 | 2.3 | Good | Good | Good | ⊚ | 2.890 |
| | 6-5 | 30.9 | 142.9 | 2.2 | 10.0 | 4.6 | Good | Good | Good | ⊚ | 2.005 |

TABLE 10-continued

| Test piece | | Content (test piece) | | Mixture solution (when measured) | | Conc. of Tween 80/ Conc. of BCP | 1) Concentration linearity | 2) Measurement sensitivity | 3) Precision (accuracy) | Evaluation | k/s value |
|---|---|---|---|---|---|---|---|---|---|---|---|
| | | BCP [µg/cm²] | Tween 80 [µg/cm²] | Conc. of BCP [µg/µL] | Conc. of Tween 80 [µg/µL] | | | | | | |
| | 6-6 | 77.2 | 178.6 | 5.4 | 12.5 | 2.3 | Good | Good | Good | ◎ | 2.944 |
| | 6-7 | 30.9 | 428.6 | 2.2 | 30.0 | 13.9 | Good | Good | Good | ◎ | 1.300 |
| | 6-8 | 30.9 | 328.6 | 2.2 | 23.0 | 10.6 | Good | Good | Good | ◎ | 1.516 |
| | 6-9 | 30.9 | 53.6 | 2.2 | 3.8 | 1.7 | Good | Good | Good | ◎ | 2.235 |
| | 6-10 | 30.9 | 35.7 | 2.2 | 2.5 | 1.2 | Good | Good | Good | ◎ | 2.388 |
| | 6-11 | 15.4 | 142.9 | 1.1 | 10.0 | 9.3 | Good | Good | Good | ◎ | 0.847 |
| | 6-12 | 3.9 | 71.4 | 0.3 | 5.0 | 18.5 | Good | Good | Poor | ○ | 0.430 |
| | 6-13 | 77.2 | 71.4 | 5.4 | 5.0 | 0.9 | Good | Good | Poor | ○ | 0.480 |
| | 6-14 | 3.9 | 8.9 | 0.3 | 0.6 | 2.3 | Good | Good | Poor | ○ | 0.469 |
| | 6-15 | 30.9 | 8.9 | 2.2 | 0.6 | 0.3 | Good | Good | Poor | ○ | 0.213 |
| Ref. Ex. | 6-1 | 0.2 | 71.4 | 0.01 | 5.0 | 462.8 | Good | Poor | Poor | X | 0.014 |
| | 6-2 | 0.2 | 0.4 | 0.01 | 0.03 | 2.3 | Good | Poor | Poor | X | 0.012 |

The evaluation results of the albumin test pieces shown in Table 10 are plotted, with the content of BCP (µg/µL) relative to the amount of the spotted sample being taken as the horizontal axis, and the content of Tween 80 (µg/µL) relative to the amount of the spotted sample being taken as the vertical axis, and the diagram obtained is shown in FIG. 15. The same evaluation results are plotted with the content of BCP (µg/cm²) per unit area of the reagent holding layer being taken as the horizontal axis, and the content of Tween 80 (µg/cm²) per unit area of the reagent holding layer being taken as the vertical axis, and the diagram obtained is shown in FIG. 16. The numerical value shown in each cell indicates the ratio of the content of Tween 80 to the content of BCP (D/C, weight ratio). In FIGS. 15 and 16, the test pieces of Examples satisfying the conditions, with the values of D/C being underlined, had K/S values of 2.2 or more when measuring the specimen 3.

As shown in Table 10 and FIGS. 15 and 16, all of the test pieces of Examples (Examples 6-1 to 6-15) as the dry test pieces containing Tween 80 as the component D had good evaluation regarding both of the evaluation items 1) and 2), which confirms that these test pieces enable the measurement of albumin at a high sensitivity. Besides, the test pieces exhibited high linearity, which proves that they enable the measurement of albumin at a high accuracy.

As shown in Table 10, regarding the dry test pieces containing Tween 80 as the component D, it was confirmed that any dry test piece satisfying the following conditions (Examples 6-1 to 6-11) enables the measurement of the concentration of albumin at a high accuracy, even if serum containing hemoglobin is measured.

D/C (Tween 80/BCP, weight ratio): 1.2 to 13.9
Concentration of BCP: 0.5 to 5.4 µg/µL (content: 7.7 to 77.2 µg/cm²)
Concentration of Tween 80: 30 µg/µL or less (content: 428.6 µg/cm² or less)

The dry test pieces of Examples 6-2 to 6-4, 6-6, 6-8, and 6-9 had K/S values of 2.2 or more when measuring the specimen 3 having a concentration of albumin of 6.5 g/dL (concentration of hemoglobin: 0 g/dL). Therefore, with the test pieces satisfying the following conditions, albumin can be measured at a higher accuracy even with respect to serum containing a large amount of hemoglobin.

D/C (Tween 80/BCP, weight ratio): 1.2 to 2.3
Concentration of BCP: 2.2 to 5.4 µg/µL
Concentration of Tween 80: 12.5 µg/µL or less As is clear from the above-described evaluation results, test pieces containing any of the following seven types of nonionic surfactants as the component D and satisfying the following condition A had good evaluation results regarding the evaluation items 1) and 2) both. Therefore, it was clarified that the test pieces containing a nonionic surfactant as the component D and satisfying the conditions A shown below enable the measurement of albumin at a high sensitivity. Besides, the test pieces exhibited high linearity, which proves that they enable the measurement of albumin at a high accuracy. In addition, the test pieces satisfying the following conditions B had good evaluation results regarding the evaluation item 3) as well. Therefore, it was clarified that the test pieces containing a nonionic surfactant as the component D and satisfying the conditions B shown below enable the measurement at a higher accuracy of the concentration of albumin in serum containing hemoglobin.

Component D:
  polyoxyethylene (23) lauryl ether (Brij 35, HLB: 16.9)
  polyoxyethylene distyrenated phenyl ether (produced by Kao Corporation, Emulgen A90, HLB: 14.5)
  polyoxyethylene (13) oleyl ether (produced by Kao Corporation, Emulgen 420, HLB: 13.6)
  polyoxyethylene polyoxypropylene alkyl ether (produced by Kao Corporation, Emulgen LS110, HLB: 13.4)
  polyoxyethylene (20) sorbitan monolaurate (Tween 20, HLB: 16.7)
  polyoxyethylene (12) lauryl ether (produced by Kao Corporation, Emulgen 120, HLB: 15.3)
  polyoxyethylene (20) sorbitan monooleate (Tween 80, HLB: 15.0)

Conditions A:
  D/C (BCP/nonionic surfactant, weight ratio): 0.3 to 13
  Concentration of the component C (BCP): 0.4 to 5.4 µg/µL (content: 5.7 to 77.2 µg/cm²)
  Concentration of the component D (nonionic surfactant): 25 µg/µL or less (content: 357.1 µg/cm² or less)

Conditions B:
  D/C (BCP/nonionic surfactant, weight ratio): 1.3 to 13
  Concentration of the component C (BCP): 0.4 to 5 µg/4 (content: 5.7 to 71.4 µg/cm²)
  Concentration of the component D (nonionic surfactant): 20 µg/µL or less (content: 285.7 µg/cm² or less)

The disclosure may be embodied in other forms without departing from the spirit or essential characteristics thereof. The embodiments disclosed in this application are to be considered in all respects as illustrative and not limiting. The scope of the disclosure is indicated by the appended claims rather than by the foregoing description, and all changes which come within the meaning and range of equivalency of the claims are intended to be embraced therein.

What is claimed is:

1. A test piece for measuring albumin contained in a sample, the test piece comprising:
 a strip-shaped support; and
 a reagent holding layer provided on the support,
 wherein the reagent holding layer contains, in a solid state, a protein denaturation agent (component A), a sulfhydryl reagent (SH reagent) (component B), bromocresol purple (component C), and a nonionic surfactant (component D),
 wherein in the reagent holding layer,
 a weight ratio (D/C) of the component D to the component C is 0.3 to 13,
 a content of the component C relative to an amount of the sample is 0.4 µg/µL to 5.4 µg/µL, and
 a content of the component D relative to the amount of the sample is 25 µg/µL or less.

2. The test piece according to claim 1,
 wherein the weight ratio (D/C) of the component D to the component C is 1.3 to 13,
 the content of the component C relative to the amount of the sample is 0.4 µg/µL to 5 µg/µL, and
 the content of the component D relative to the amount of the sample is 20 µg/µL or less.

3. The test piece according to claim 1,
 wherein the nonionic surfactant is a nonionic surfactant having a polyoxyethylene group.

4. The test piece according to claim 1,
 wherein the nonionic surfactant has a hydrophilic-lipophilic balance (HLB) value of 13.4 to 16.9.

5. The test piece according to claim 1,
 wherein the nonionic surfactant is at least one selected from the group consisting of polyoxyethylene (23) lauryl ether, polyoxyethylene distyrenated phenyl ether, polyoxyethylene (13) oleyl ether, polyoxyethylene polyoxypropylene alkyl ether, polyoxyethylene (20) sorbitan monolaurate, polyoxyethylene (12) lauryl ether, and polyoxyethylene (20) sorbitan monooleate.

6. The test piece according to claim 1,
 wherein the component D is polyoxyethylene (23) lauryl ether,
 the weight ratio (D/C) of the component D to the component C is 1.3 to 13,
 the content of the component C relative to the amount of the sample is 0.4 µg/µL to 5 µg/µL, and
 the content of the component D relative to the amount of the spotted sample is 20 µg/µL or less.

7. The test piece according to claim 1,
 wherein the component D is polyoxyethylene distyrenated phenyl ether,
 the weight ratio (D/C) of the component D to the component C is 1.2 to 10.6, and
 the content of the component C relative to the amount of the sample is 0.5 µg/µL to 5.4 µg/µL.

8. The test piece according to claim 1,
 wherein the component D is polyoxyethylene (13) oleyl ether,
 the weight ratio (D/C) of the component D to the component C is 0.9 to 9.3, and
 the content of the component C relative to the amount of the spotted sample is 0.5 µg/µL to 5.4 µg/µL.

9. The test piece according to claim 1,
 wherein the component D is polyoxyethylene polyoxypropylene alkyl ether,
 the weight ratio (D/C) of the component D to the component C is 1.2 to 2.3, and
 the content of the component C relative to the amount of the sample is 2.2 µg/µL to 5.4 µg/µL.

10. The test piece according to claim 1,
 wherein the component D is polyoxyethylene (20) sorbitan monolaurate,
 the weight ratio (D/C) of the component D to the component C is 1.7 to 2.3, and
 the content of the component C relative to the amount of the spotted sample is 2.2 µg/µL to 4.3 µg/µL.

11. The test piece according to claim 1,
 wherein the component D is polyoxyethylene (12) lauryl ether,
 the weight ratio (D/C) of the component D to the component C is 1.2 to 2.3, and
 the content of the component C relative to the amount of the spotted sample is 2.2 µg/µL to 4.3 µg/µL.

12. The test piece according to claim 1,
 wherein the protein denaturation agent is an anionic surfactant.

13. The test piece according to claim 1,
 wherein the sample is a biological specimen.

14. The test piece according to claim 13,
 wherein the biological specimen is serum or plasma.

15. The test piece according to claim 1,
 wherein the reagent holding layer is obtained by impregnating a porous substance or a fibrous substance with a reagent solution containing the protein denaturation agent, the sulfhydryl reagent, the bromocresol purple, and the nonionic surfactant and drying the reagent solution.

16. The test piece according to claim 1,
 wherein the reagent holding layer is made by directly providing a reagent solution containing the protein denaturation agent, the sulfhydryl reagent, the bromocresol purple, and the nonionic surfactant on the support and drying the reagent solution.

17. A test piece for measuring albumin contained in a sample, the test piece comprising:
 a strip-shaped support; and
 a reagent holding layer provided on the support,
 wherein the reagent holding layer contains, in a solid state, a protein denaturation agent (component A), a sulfhydryl reagent (SH reagent) (component B), bromocresol purple (component C), and a nonionic surfactant (component D), and
 the component D is polyoxyethylene (20) sorbitan monooleate,
 wherein in the reagent holding layer,
 a weight ratio (D/C) of the component D to the component C is 1.2 to 13.9,
 a content of the component C relative to an amount of the sample is 0.5 µg/µL to 5.4 µg/µL, and
 a content of the component D relative to the amount of the sample is 30 µg/µL or less.

18. A method for measuring an amount of albumin in a sample based on measured values of optical properties of bromocresol purple in the presence of a protein denaturation agent and an SH reagent, the method comprising:
 spotting a predetermined amount of the sample on a reagent holding layer of a test piece, the reagent holding layer containing, in a solid state, the protein denaturation agent (component A), a sulfhydryl reagent (SH reagent) (component B), bromocresol purple (component C), and a nonionic surfactant (component D), forming a mixture solution in which the sample, the component A, the component B, the component C, and the component D are mixed, wherein in the mixture solution, a weight ratio (D/C) of the component D to the component C is 0.3 to 13, a concentration of the component C is 0.4 µg/µL to 5.4 µg/µL, and a concentration of the component D is 25 µg/µL or less.

19. The method according to claim 18, wherein the test piece comprises a support; and the reagent holding layer is provided on the support, wherein in the reagent holding layer, a weight ratio (D/C) of the component D to the component C is 0.3 to 13, a content of the component C relative to the predetermined amount of the sample is 0.4 µg/µL to 5.4 g/µL, and a content of the component D relative to the predetermined amount of the sample is 25 µg/µL or less.

20. The method according to claim 18, wherein the protein denaturation agent is an anionic surfactant.

21. The method according to claim 18, wherein the sample is a biological specimen.

22. The method according to claim 21, wherein the biological specimen is serum or plasma.

\* \* \* \* \*